US012102458B2

(12) United States Patent
Inazawa

(10) Patent No.: US 12,102,458 B2
(45) Date of Patent: Oct. 1, 2024

(54) REUSABLE MEDICAL BOX

(71) Applicant: TEIJIN LIMITED, Osaka (JP)

(72) Inventor: Yasunori Inazawa, Osaka (JP)

(73) Assignee: TEIJIN LIMITED, Osaka (JP)

( * ) Notice: Subject to any disclaimer, the term of this patent is extended or adjusted under 35 U.S.C. 154(b) by 1105 days.

(21) Appl. No.: 16/964,276

(22) PCT Filed: Jan. 22, 2019

(86) PCT No.: PCT/JP2019/001912
§ 371 (c)(1),
(2) Date: Jul. 23, 2020

(87) PCT Pub. No.: WO2019/146606
PCT Pub. Date: Aug. 1, 2019

(65) Prior Publication Data
US 2021/0030507 A1    Feb. 4, 2021

(30) Foreign Application Priority Data

Jan. 24, 2018  (JP) ................................. 2018-009661

(51) Int. Cl.
*A61B 50/36*    (2016.01)
*C08L 9/06*    (2006.01)
(Continued)

(52) U.S. Cl.
CPC ................ *A61B 50/36* (2016.02); *C08L 9/06* (2013.01); *C08L 23/12* (2013.01); *C08L 53/005* (2013.01); *C08L 69/00* (2013.01); *C08L 2207/53* (2013.01)

(58) Field of Classification Search
CPC .......... C08L 9/06; C08L 23/02; C08L 53/005; C08L 69/00; A61B 50/36; A61J 1/00; Y02W 30/00
(Continued)

(56) References Cited

U.S. PATENT DOCUMENTS 4,122,131 A    10/1978  Bussink et al.
5,021,504 A     6/1991  Fujita et al.
(Continued)

FOREIGN PATENT DOCUMENTS

CN    101724239    6/2010
CN    102993668    3/2013
(Continued)

OTHER PUBLICATIONS

International Search Report issued Feb. 26, 2019 in International (PCT) Application No. PCT/JP2019/001912.
(Continued)

*Primary Examiner* — Tri V Nguyen
(74) *Attorney, Agent, or Firm* — Wenderoth, Lind & Ponack, L.L.P.

(57) ABSTRACT

The present invention provides a reusable medical box which has excellent mechanical properties, chemical resistance, heat resistance, and needle-penetration resistance. The medical box of the present invention is a reusable medical box consisting of a polycarbonate resin composition comprising, based on a total of 100 parts by weight of (A) a polycarbonate-based resin (component A) and (B) a polyolefin-based resin (component B), 1 to 30 parts by weight of (C) a styrene-based thermoplastic elastomer (component C).

9 Claims, 1 Drawing Sheet

(51) Int. Cl.
*C08L 23/12* (2006.01)
*C08L 53/00* (2006.01)
*C08L 69/00* (2006.01)

(58) Field of Classification Search
USPC ........................................................ 428/35.5
See application file for complete search history.

(56) References Cited

U.S. PATENT DOCUMENTS

| | | | |
|---|---|---|---|
| 5,145,063 A | | 9/1992 | Lee |
| 5,516,920 A | | 5/1996 | Nesvadba et al. |
| 6,231,965 B1 | | 5/2001 | Takemura et al. |
| 2009/0032423 A1* | | 2/2009 | Japuntich ............... A61B 42/40 220/23.83 |

FOREIGN PATENT DOCUMENTS

| | | |
|---|---|---|
| CN | 105237981 | 1/2016 |
| JP | 54-53162 | 4/1979 |
| JP | 63-215750 | 9/1988 |
| JP | 63-215752 | 9/1988 |
| JP | 64-75543 | 3/1989 |
| JP | 64-75544 | 3/1989 |
| JP | 5-17633 | 1/1993 |
| JP | 5-306336 | 11/1993 |
| JP | 6-172508 | 6/1994 |
| JP | 7-233160 | 9/1995 |
| JP | 7-330972 | 12/1995 |
| JP | 8-27370 | 1/1996 |
| JP | 8-134277 | 5/1996 |
| JP | 10-314242 | 12/1998 |
| JP | 2000-017120 | 1/2000 |
| JP | 2001-055435 | 2/2001 |
| JP | 2002-117580 | 4/2002 |
| JP | 2002-0291814 | 10/2002 |
| JP | 2005-132937 | 5/2005 |
| JP | 2009-142404 | 7/2009 |
| JP | 2009-535163 | 10/2009 |
| JP | 2014-181323 | 9/2014 |
| JP | 2015-203098 | 11/2015 |
| JP | 2016-113480 | 6/2016 |
| JP | 2016-130291 | 7/2016 |
| JP | 2016-147978 | 8/2016 |
| WO | 2007/130402 | 11/2007 |
| WO | 2016/100660 | 6/2016 |

OTHER PUBLICATIONS

Website; Wikipedia "Polycarbonate", edited Jun. 23, 2022, https://en.wikipedia.org/wiki/Polycarbonate#:~:text=Polycarbonates%20(PC)%20are%20a%20group,worked%2C%20molded%2C%20and%20thermoformed, cited in Office Action of counterpart application.
Website; Total Materia "Charpy Impact Steel Testing: Part One", Mar. 2019. https://www.totalmateria.com/page.aspx?ID=CheckArticle&site=kts&NM=534, cited in Office Action of counterpart application.
Website; Prospector "Polycarbonate—an overview", Feb. 26, 2021, https://knowledge.ulprospector.com/11442/pe-polycarbonate-anverview/#:~:text-Polycarbonate%20maintains20its%20properties%20over,above%20about%20155%C2%B0C, cited in Office Action of counterpart application.

* cited by examiner

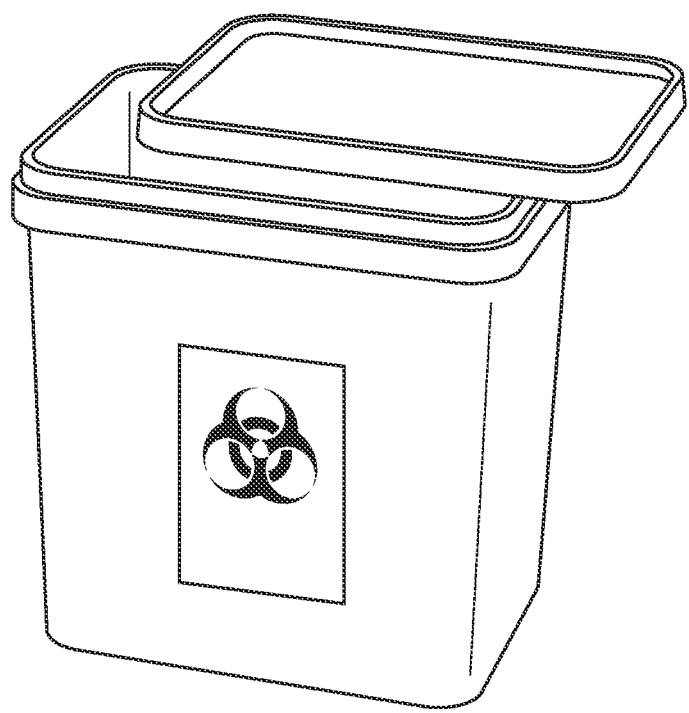

REUSABLE MEDICAL BOX

TECHNICAL FIELD

The present invention relates to a reusable medical box consisting of a polycarbonate resin composition. More specifically, the present invention relates to a reusable medical box which consists of a resin composition comprising a polycarbonate-based resin, a polyolefin-based resin, and a styrene-based thermoplastic elastomer and which has excellent mechanical properties, chemical resistance, heat resistance, and needle-penetration resistance.

BACKGROUND

A polycarbonate resin is widely used in a variety of fields such as OA equipment, electronic and electric equipment, and automobiles as it has excellent mechanical properties and thermal properties. However, the polycarbonate resin has low workability due to high melt viscosity and has a problem with chemical resistance especially to cleaners as it is an amorphous resin. Therefore, it is known that a polyolefin-based resin is added to the polycarbonate resin to compensate for these disadvantages. When a polyolefin-based resin is simply added to the polycarbonate resin, delamination etc., occurs due to low compatibility between the polycarbonate resin and the polyolefin-based resin, thereby making it difficult to obtain satisfactory mechanical properties. Therefore, it is difficult to put it to practical use.

Then, to enhance compatibility between the polycarbonate resin and the polyolefin-based resin so as to provide mechanical properties for practical use, various resin compositions are proposed. For example, there is disclosed a process in which an elastomer graft modified with a hydroxyl group-containing vinyl monomer is added as a compatibilizer (refer to Patent Documents 1 and 2). There is also disclosed a process in which polypropylene modified with a hydroxyl group-containing vinyl monomer is used as a compatibilizer and an ethylene-α-olefin copolymer of ethylene and an α-olefin having 4 or more carbon atoms is used as an impact resisting agent (refer to Patent Documents 3 and 4). There is further disclosed a process in which a terminal carboxylated polycarbonate resin and an epoxylated polypropylene resin are used (refer to Patent Document 5). There is still further disclosed a process in which a terminal carboxylated polycarbonate resin and a maleic anhydride-modified polypropylene resin are used (refer to Patent Document 6). There is still further disclosed a process in which a styrene-ethylene/butylene-styrene block copolymer is added as a compatibilization agent (refer to Patent Literature 7) and a method in which a styrene-ethylene/propylene-styrene copolymer is added (refer to Patent Literature 8) are known.

Currently, most medical boxes are used one time and are incinerated after use, and conventionally, cardboard and polypropylene resins are often used. Thus, medical accidents such as injection needles penetrating the container and stabbing a person have occurred, and such containers are insufficient from the viewpoint of safety. Furthermore, in order to reuse a medical box, it is necessary that the medical box be capable of being used without deformation due to heat and load and without significant deterioration of the resin after sterilization and washing processes are carried out at high temperatures and high humidity with an autoclave, and thus, particularly from the viewpoint of heat resistance, the above materials do not withstand repeated use due to the autoclave sterilization (refer to Patent Literature 9 and 10).

RELATED ART

Patent Literature

[PTL 1] Japanese Unexamined Patent Publication (Kokai) JPH07-330972A
[PTL 2] Japanese Unexamined Patent Publication (Kokai) JPH08-134277A
[PTL 3] Japanese Unexamined Patent Publication (Kokai) JP2005-132937A
[PTL 4] Japanese Unexamined Patent Publication (Kokai) JPS54-53162A
[PTL 5] Japanese Unexamined Patent Publication (Kokai) JPS63-215750A
[PTL 6] Japanese Unexamined Patent Publication (Kokai) JPS63-215752A
[PTL 7] Japanese Unexamined Patent Publication (Kokai) JPH05-17633A
[PTL 8] Japanese Unexamined Patent Publication (Kokai) JP2000-17120A
[PTL 9] Japanese Unexamined Patent Publication (Kokai) JP2002-291814A
[PTL 10] Japanese Unexamined Patent Publication (Kokai) JPH10-314242A

SUMMARY

Problems to be Solved by the Invention

The object of the present invention is to provide a novel and useful medical box.

Solution to the Problem

The present inventors have discovered that when a medical box is produced using a polycarbonate resin composition comprising a polycarbonate-based resin, a polyolefin-based resin, and a styrene-based thermoplastic elastomer, a reusable medical box which achieves high levels of mechanical properties, chemical resistance, heat resistance, and needle-penetration resistance can be obtained.

Specifically, though autoclave sterilization cannot be performed in the case in which cardboard, polypropylene resin, etc., are used, as in the prior art, from the viewpoint of heat resistance, when the polycarbonate resin composition used in the present invention is adopted, since the heat resistance thereof is high, treatment thereof can be carried out, whereby a reusable medical box can be provided. Furthermore, even if a medical box is simply manufactured using a resin having a high heat resistance, a medical box that can withstand practical use in terms of chemical resistance, needle-penetration resistance, etc., cannot be provided. However, it has been found that the medical box of the present invention has such characteristics.

According to the present invention, the above problems can be solved by the medical box of the following aspects:

Embodiment 1

A medical box consisting of a polycarbonate resin composition comprising, based on a total of 100 parts by weight of (A) a polycarbonate-based resin (component A) and (B)

a polyolefin-based resin (component B), 1 to 30 parts by weight of (C) a styrene-based thermoplastic elastomer (component C);

Embodiment 2

The medical box according to embodiment 1, wherein the content of styrene units of the component C is 40 to 80 wt %;

Embodiment 3

The medical box according to embodiment 1 or 2, wherein the component B is a polypropylene-based resin;

Embodiment 4

The medical box according to any one of embodiments 1 to 3, wherein a hydrogenated polydiene unit in the component C is a hydrogenated isoprene unit and is a block copolymer having an ethylene-propylene block unit;

Embodiment 5

The medical box according to any one of embodiments 1 to 3, wherein a hydrogenated polydiene unit in the component C is a hydrogenated butadiene unit and is a block copolymer having an ethylene-butylene block unit;

Embodiment 6

The medical box according to any one of embodiments 1 to 3, wherein a hydrogenated polydiene unit in the component C is a partially-hydrogenated butadiene unit and is a block copolymer having a butadiene-butylene block unit;

Embodiment 7

The medical box according to any one of embodiments 1 to 6, wherein the content of the component B is 5 to 50 parts by weight in a total 100 parts by weight of the component A and the component B;

Embodiment 8

The medical box according to any one of embodiments 1 to 7, further comprising, based on a total of 100 parts by weight of the component A and the component B, 1 to 10 parts by weight of (D) a core-shell type graft polymer (component D);

Embodiment 9

The medical box according to any one of embodiments 1 to 8, wherein the MFR of the component B and the component C at 230° C. under a load of 2.16 kg is 0.1 to 10 g/10 min and the ratio of the MFR of the component B and the component C (MFR of the component B/MFR of the component C) is 0.5 to 10.

Advantageous Effects of Invention

Since the medical box consisting of the polycarbonate resin composition of the present invention achieves high levels of mechanical properties, chemical resistance, heat resistance, and needle-penetration resistance, it can be used repeatedly by autoclaving and is very useful for reducing environmental impact and building a sustainable society. Furthermore, since accident such as a used injection needle penetrating the container and stabbing a person can be prevented, an effect can be expected in terms of safety. Thus, the industrial effects of the present invention are extremely significant.

BRIEF DESCRIPTION OF DRAWINGS

FIG. 1 illustrates an aspect of the medical box of the present invention.

DESCRIPTION OF EMBODIMENTS

The details of the present invention will be described below.

<Component A: Polycarbonate-Based Resin>

The polycarbonate-based resin used in the present invention is obtained by reacting a dihydric phenol with a carbonate precursor. Examples of the reaction include interfacial polycondensation, melt transesterification, the solid-phase transesterification of a carbonate prepolymer and the ring-opening polymerization of a cyclic carbonate compound.

Typical examples of the dihydric phenol used herein include hydroquinone, resorcinol, 4,4'-biphenol, 1,1-bis(4-hydroxyphenyl)ethane, 2,2-bis(4-hydroxyphenyl)propane (commonly known as "bisphenol A"), 2,2-bis(4-hydroxy-3-methylphenyl)propane, 2,2-bis(4-hydroxyphenyl)butane, 1,1-bis(4-hydroxyphenyl)-1-phenylethane, 1,1-bis(4-hydroxyphenyl)cyclohexane, 1,1-bis(4-hydroxyphenyl)-3,3,5-trimethylcyclohexane, 2,2-bis(4-hydroxyphenyl)pentane, 4,4'-(p-phenylenediisopropylidene)diphenol, 4,4'-(m-phenylenediisopropylidene)diphenol, 1,1-bis(4-hydroxyphenyl)-4-isopropylcyclohexane, bis(4-hydroxyphenyl)oxide, bis(4-hydroxyphenyl)sulfide, bis(4-hydroxyphenyl)sulfexide, bis(4-hydroxyphenyl)sulfone, bis(4-hydroxyphenyl)ketone, bis(4-hydroxyphenyl)ester, bis(4-hydroxy-3-methylphenyl)sulfide, 9,9-bis(4-hydroxyphenyl)fluorene and 9,9-bis(4-hydroxy-3-methylphenyl)fluorene. Out of these dihydric phenols, bis(4-hydroxyphenyl)alkanes are preferred, and bisphenol A is particularly preferred from the viewpoint of impact resistance and commonly used.

In the present invention, besides bisphenol A-based polycarbonates which are general-purpose polycarbonates, special polycarbonates which are produced by using another dihydric phenol may be used as the component A.

For example, polycarbonates (homopolymers or copolymers) obtained by using 4,4'-(m-phenylenediisopropylidene)diphenol (may be abbreviated as "BPM" hereinafter), 1,1-bis(4-hydroxyphenyl)cyclohexane, 1,1-bis(4-hydroxyphenyl)-3,3,5-trimethylcyclohexane (may be abbreviated as "Bis-TMC" hereinafter), 9,9-bis(4-hydroxyphenyl)fluorene and 9,9-bis(4-hydroxy-3-methylphenyl)fluorene (may be abbreviated as "BCF" hereinafter) as part or all of the dihydric phenol component are suitable for use in fields in which the requirements for dimensional stability and form stability against water absorption are very strict. These dihydric phenols except for BPA are used in an amount of preferably not less than 5 mol %, particularly preferably not less than 10 mol % of the whole dihydric phenol component constituting the polycarbonate.

Particularly when high stiffness and excellent resistance to hydrolysis are required, the component A constituting the resin composition is particularly preferably one of the following copolycarbonates (1) to (3).

(1) A copolycarbonate which comprises 20 to 80 mol % (preferably 40 to 75 mol %, more preferably 45 to 65 mol %) of BPM and 20 to 80 mol % (preferably 25 to 60 mol; more preferably 35 to 55 mol %) of BCF based on 100 mol % of the dihydric phenol component constituting the polycarbonate.

(2) A copolycarbonate which comprises 10 to 95 mol % (preferably 50 to 90 mol %, more preferably 60 to 85 mol %) of BPA and 5 to 90 mol % (preferably 10 to 50 mol %, more preferably 15 to 40 mol %) of BCF based on 100 mol % of the dihydric phenol component constituting the polycarbonate.

(3) A copolycarbonate which comprises 20 to 80 mol % (preferably 40 to 75 mol %, more preferably 45 to 65 mon) of BPM and 20 to 80 mol % (preferably 25 to 60 mol %, more preferably 35 to 55 mol %) of Bis-TMC based on 100 mol % of the dihydric phenol component constituting the polycarbonate.

These special polycarbonates may be used alone or in combination of two or more. They may be used by mixing with a commonly used bisphenol A type polycarbonate.

The production processes and characteristic properties of these special polycarbonates are detailed in, for example, JP-H06-172508A, JP-H08-27370A, JP-2001-55435A and JP2002-117580A.

Out of the above polycarbonates, polycarbonates whose water absorption coefficient and Tg (glass transition temperature) have been adjusted to the following ranges by controlling their copolymer compositions are excellent in the hydrolysis resistance of the polymer itself and rarely warp after molding. Therefore, they are particularly preferred in fields in which dimensional stability is required.

(i) A polycarbonate having a water absorption coefficient of 0.05 to 0.15%, preferably 0.06 to 0.13% and a Tg of 120 to 180° C., or (ii) a polycarbonate having a Tg of 160 to 250° C., preferably 170 to 230° C. and a water absorption coefficient of 0.10 to 0.30%, preferably 0.13 to 0.30%, more preferably 0.14 to 0.27%.

The water absorption coefficient of a polycarbonate is a value obtained by measuring the moisture content of a disk-like test piece having a diameter of 45 mm and a thickness of 3.0 mm after the test piece is immersed in 23° C. water for 24 hours in accordance with ISO62-1980. Tg (glass transition temperature) is a value obtained by measurement with a differential scanning calorimeter (DSC) in accordance with JIS K7121.

The carbonate precursor is a carbonyl halide, diester carbonate or haloformate, as exemplified by phosgene, diphenyl carbonate and dihaloformates of a dihydric phenol.

For the manufacture of an aromatic polycarbonate resin by the interfacial polymerization of a dihydric phenol and a carbonate precursor, a catalyst, an end sealing agent and an antioxidant for preventing the oxidation of the dihydric phenol may be optionally used. The polycarbonate resin of the present invention includes a branched polycarbonate resin obtained by copolymerizing a polyfunctional aromatic compound having 3 or more functional groups, a polyester carbonate resin obtained by copolymerizing an aromatic or aliphatic (including alicyclic) bifunctional carboxylic acid, a copolycarbonate resin obtained by copolymerizing a bifunctional alcohol (including an alicyclic bifunctional alcohol), and a polyester carbonate resin obtained by copolymerizing the bifunctional carboxylic acid and the bifunctional alcohol. It may also be a mixture of two or more of the obtained aromatic polycarbonate resins.

The branched polycarbonate resin can provide dripping preventing performance etc., to the resin composition of the present invention. Examples of the polyfunctional aromatic compound having 3 or more functional groups used in the branched polycarbonate resin include phloroglucin, phloroglucide, 4,6-dimethyl-2,4,6-tris(4-hydroxydiphenyl)heptene-2, 2,4,6-trimethyl-2,4,6-tris(4-hydroxyphenyl)heptane, 1,3,5-tris(4-hydroxyphenyl)benzene, 1,1,1-tris(4-hydroxyphenyl)ethane, 1,1,1-tris(3,5-dimethyl-4-hydroxyphenyl)ethane, 2,6-his(2-hydroxy-5-methylbenzyl)-4-methylphenol and 4-{4-[1,1-bis(4-hydroxyphenyl)ethyl]benzene}α,αdimethylbenzylphenol and other trisphenols, tetra(4-hydroxyphenyl)methane, bis(2,4-dihydroxyphenyl)ketone, 1,4-bis(4,4-dihydroxytriphenylmethyl)benzene, trimellitic acid, pyromellitic acid, benzophenone tetracarboxylic acid and acid chlorides thereof. Out of these, 1,1,1-tris(4-hydroxyphenyl)ethane and 1,1,1-tris(3,5-dimethyl-4-hydroxyphenyl)ethane are preferred, and 1,1,1-tris(4-hydroxyphenyl)ethane is particularly preferred.

The content of a constituent unit derived from the polyfunctional aromatic compound in the branched polycarbonate is preferably 0.01 to 1 mol %, more preferably 0.05 to 0.9 mol %, much more preferably 0.05 to 0.8 mol % based on 100 mol % of the total of a constituent unit derived from the dihydric phenol and the constituent unit derived from the polyfunctional aromatic compound.

In particular in the case of the melt transesterification process, a branched structure unit may be produced as a side reaction. The content of the branched structure unit is preferably 0.001 to 1 mol %, more preferably 0.005 to 0.9 mol %, much more preferably 0.01 to 0.8 mol % based on 100 mol % of the total of this unit and the constituent unit derived from the dihydric phenol. The content of the branched structure can be calculated by 1H-NMR measurement.

The aliphatic bifunctional carboxylic acid is preferably α,ω-dicarboxylic acid. Preferred examples of the aliphatic bifunctional carboxylic acid include linear saturated aliphatic dicarboxylic acids such as sebacic acid (decanedioic acid), dodecanedioic acid, tetradecanedioic acid, octadecanedioic acid and icosanedioic acid, and alicyclic dicarboxylic acids such as cyclohexanedicarboxylic acid. The bifunctional alcohol is preferably an alicyclic diol such as cyclohexanedimethanol, cyclohexanediol or tricyclodecanedimethanol.

Reaction systems for producing a polycarbonate-based resin of the present invention, such as interfacial polymerization, melt transesterification, the solid-phase transesterification of a carbonate prepolymer or the ring-opening polymerization of a cyclic carbonate compound, are well known through documents and patent publications.

For the manufacture of the resin composition of the present invention, the viscosity average molecular weight (M) of the polycarbonate-based resin is not limited but preferably $1.8 \times 10^4$ to $4.0 \times 10^4$, more preferably $2.0 \times 10^4$ to $3.5 \times 10^4$, much more preferably $2.2 \times 10^4$ to $3.0 \times 10^4$. When the viscosity average molecular weight is within a proper range, good mechanical properties and good fluidity at the time of injection molding may be obtained.

The polycarbonate-based resin may be obtained by mixing a polycarbonate-based resin having a viscosity average molecular weight outside the above range. Particularly a polycarbonate-based resin having a viscosity average molecular weight higher than the above range ($5.0 \times 10^4$) improves the entropy elasticity of a resin. As a result, it exhibits high moldability in gas assist molding and foam molding which are used to form a reinforced resin material into a structural member. The moldability improvement of this polycarbonate is higher than that of the above branched polycarbonate. As a more preferred example, a polycarbonate-based resin (component A-1-1) (maybe referred to as "high-molecular weight component-containing polycarbonate-based resin" hereinafter) which consists of a polycarbonate-based resin having a viscosity average molecular weight of $7 \times 10^4$ to $3 \times 10^5$ (component A-1-1-1) and an aromatic polycarbonate resin having a viscosity average molecular weight of $1 \times 10^4$ to $3 \times 10^4$ (component A-1-1-2) and has a viscosity average molecular weight of $1.6 \times 10^4$ to $3.5 \times 10^4$ may also be used as the component A.

In the above high-molecular weight component-containing polycarbonate-based resin (component. A-1-1), the molecular weight of the component A-1-1-1 is preferably $7 \times 10^4$ to $2 \times 10^5$, more preferably $8 \times 10^4$ to $2 \times 10^5$, much more preferably $1 \times 10^5$ to $2 \times 10^5$, particularly preferably $1 \times 10^5$ to $1.6 \times 10^5$. The molecular weight of the component A-1-1-2 is preferably $1 \times 10^4$ to $2.5 \times 10^4$, more preferably $1.1 \times 10^4$ to $2.4 \times 10^4$, much more preferably $1.2 \times 10^4$ to $2.4 \times 10^4$, particularly preferably $1.2 \times 10^4$ to $2.3 \times 10^4$.

The high-molecular weight component-containing polycarbonate-based resin (component A-1-1) can be obtained by mixing together the above components A-1-1-1 and A-1-1-2 in various ratios and adjusting the ratio to satisfy a predetermined molecular weight range. The content of the component A-1-1-1 is preferably 2 to 40 wt %, more preferably 3 to 30 wt %, much more preferably 4 to 20 wt %, particularly preferably 5 to 20 wt % based on 100 wt % of the component A-1-1.

To prepare the component A-1-1, (1) a method in which the component A-1-1-1 and the component A-1-1-2 are polymerized independently and mixed together, (2) a method in which an aromatic polycarbonate resin is produced by employing a method of producing an aromatic polycarbonate resin showing a plurality of polymer peaks in a molecular weight distribution chart by a GPC process as typified by the method disclosed by JP-H05-306336A in the same system to ensure that the aromatic polycarbonate resin satisfies the conditions of the component A-1-1 of the present invention, or (3) a method in which the aromatic polycarbonate resin obtained by the above production method (2) is mixed with the component A-1-1-1 and/or the component A-1-1-2 produced separately may be employed.

Regarding the viscosity average molecular weight of the present invention, a specific viscosity ($\eta_{sp}$) is obtained from a solution prepared by dissolving 0.7 g of the polycarbonate-based resin in 100 ml of methylene chloride at 20° C. with an Ostwald viscometer based on the following equation:

Specific viscosity $(\eta_{sp}) = (t - t_0)/t_0$

[$t_0$ is a time (seconds) required for the dropping of methylene chloride and t is a time (seconds) required for the dropping of a sample solution]

and then the viscosity average molecular weight M is calculated based on the following equation:

$\eta_{sp}/c = [\eta] + 0.45 \times [\eta]^2 c$ ([$\eta$] is viscosity)

$[\eta] = 1.23 \times 10^{-4} M^{0.83}$ $c = 0.7$.

The viscosity average molecular weight of the polycarbonate-based resin in the polycarbonate resin composition of the present invention is calculated by the following procedure. That is, the composition is mixed with methylene chloride in a weight ratio of 1:20 to 1:30 to dissolve soluble matter contained in the composition. The soluble matter is collected by celite filtration. Thereafter, the solvent contained in the obtained solution is removed. After the removal of the solvent, solid matter is dried completely so as to obtain a methylene chloride-soluble solid. The specific viscosity at 20° C. is obtained as described above from a solution prepared by dissolving 0.7 g of the solid in 100 ml of methylene chloride so as to calculate the viscosity average molecular weight M therefrom as described above.

A polycarbonate-polydiorganosiloxane copolymer resin may also be used as the polycarbonate-based resin (component A) of the present invention. The polycarbonate-polydiorganosiloxane copolymer resin is preferably a copolymer resin prepared by copolymerizing a dihydric phenol represented by the following general formula (1) and a hydroxyaryl-terminated polydiorganosiloxane represented by the following general formula (3).

[Chem 1]

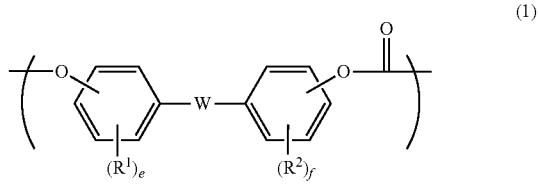

(1)

[In the above general formula (1), $R^1$ and $R^2$ are each independently a group selected from the group consisting of hydrogen atom, halogen atom, alkyl group having 1 to 18 carbon atoms, alkoxy group having 1 to 18 carbon atoms, cycloalkyl group having 6 to 20 carbon atoms, cycloalkoxy group having 6 to 20 carbon atoms, alkenyl group having 2 to 10 carbon atoms, aryl group having 6 to 14 carbon atoms, aryloxy group having 6 to 14 carbon atoms, aralkyl group having 7 to 20 carbon atoms, aralkyloxy group having 7 to 20 carbon atoms, nitro group, aldehyde group, cyano group and carboxyl group, when there are a plurality of $R^1$'s and a plurality of $R^2$'s, they may be the same or different, "e" and "f" are each an integer of 1 to 4, and W is a single bond or at least one group selected from the group consisting of groups represented by the following general formulas (2).

[Chem 2]

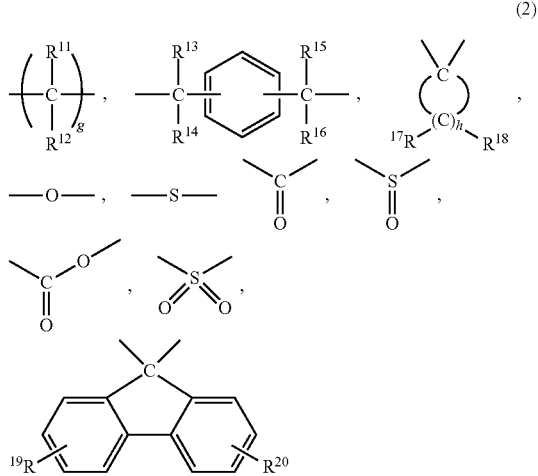

(2)

[In the above formulas (2), $R^{11}$, $R^{12}$, $R^{13}$, $R^{14}$, $R^{15}$, $R^{16}$, $R^{17}$ and $R^{18}$ are each independently a group selected from the group consisting of hydrogen atom, alkyl group having 1 to 18 carbon atoms, aryl group having 6 to 14 carbon atoms and aralkyl group having 7 to 20 carbon atoms, $R^{19}$ and $R^{20}$ are each independently a group selected from the group consisting of hydrogen atom, halogen atom, alkyl group having 1 to 18 carbon atoms, alkoxy group having 1 to 10 carbon atoms, cycloalkyl group having 6 to 20 carbon atoms, cycloalkoxy group having 6 to 20 carbon atoms, alkenyl group having 2 to 10 carbon atoms, aryl group having 6 to 14 carbon atoms, aryloxy group having 6 to 10 carbon atoms, aralkyl group having 7 to 20 carbon atoms, aralkyloxy group having 7 to 20 carbon atoms, nitro group, aldehyde group, cyano group and carboxyl group, and, regarding each of $R^{11}$ to $R^{19}$, when there are plurality of them, they may be the same or different; "g" is an integer of 1 to 10, and "h" is an integer of 4 to 7.]

[Chem 3]

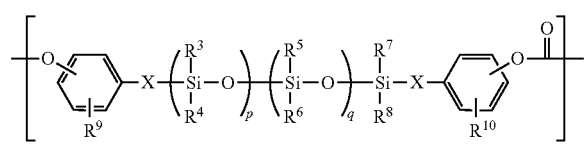

(3)

[In the above formula (3), $R^3$, $R^4$, $R^5$, $R^6$, $R^7$ and $R^8$ are each independently a hydrogen atom, alkyl group having 1 to 12 carbon atoms, or substituted or nonsubstituted aryl group having 6 to 12 carbon atoms, $R^9$ and $R^{10}$ are each independently a hydrogen atom, halogen atom, alkyl group having 1 to 10 carbon atoms or alkoxy group having 1 to 10 carbon atoms, "p" is a natural number, "q" is 0 or natural number, and (p+q) is a natural number of 10 to 300. X is a divalent aliphatic group having 2 to 8 carbon atoms.]

Examples of the dihydric phenol (I) represented by the general formula (1) include 4,4'-dihydroxybiphenyl, bis(4-hydroxyphenyl)methane, 1,1-bis(4-hydroxyphenyl)ethane, 1,1-bis(4-hydroxyphenyl)-1-phenylethane, 2,2-bis(4-hydroxyphenyl)propane, 2,2-bis(4-hydroxy-3-methylphenyl) propane, 1,1-bis(4-hydroxyphenyl)-3,3,5-trimethylcyclohexane, 2,2-bis(4-hydroxy-3,3'-biphenyl)propane, 2,2-bis (4-hydroxy-3-isopropylphenyl)propane, 2,2-bis(3-t-butyl-4-hydroxyphenyl)propane, 2,2-bis(4-hydroxyphenyl)butane, 2,2-bis(4-hydroxyphenyl)octane, 2,2-bis(3-bromo-4-hydroxyphenyl)propane, 2,2-bis(3,5-dimethyl-4-hydroxyphenyl)propane, 2,2-bis(3-cyclohexyl-4-hydroxyphenyl)propane, 1,1-bis(3-cyclohexyl-4-hydroxyphenyl)cyclohexane, bis(4-hydroxyphenyl)diphenylmethane, 9,9-bis(4-hydroxyphenyl)fluorene, 9,9-bis(4-hydroxy-3-methylphenyl)fluorene, 1,1-bis(4-hydroxyphenyl)cyclohexane, 1,1-bis(4-hydroxyphenyl)cyclopentane, 4,4'-dihydroxydiphenyl ether, 4,4'-dihydroxy-3,3'-dimethyldiphenyl ether, 4,4'-sulfonyldiphenol, 4,4'-dihydroxydiphenyl sulfoxide, 4,4'-dihydroxydiphenyl sulfide, 2,2'-dimethyl-4,4'-sulfonyldiphenol, 4,4'-dihydroxy-3,3'-dimethyldiphenyi sulfoxide, 4,4'-dihydroxy-3, 3'-dimethyldiphenyl sulfide, 2,2'-diphenyl-4,4'-sulfonyl diphenyl, 4,4'-dihydroxy-3,3'-diphenyldiphenyl sulfoxide, 4,4'-dihydroxy-3,3'-diphenyldiphenyi sulfide, 1,3-bis{2-(4-hydroxyphenyl)propyl}benzene, 1,4-bis{2-(4-hydroxyphenyl)propyl}benzene, 1,4-bis(4-hydroxyphenyl)cyclohexane, 1,3-bis(4-hydroxyphenyl)cyclohexane, 4,8-bis(4-hydroxyphenyl)tricyclo[5.2.1.02,6]decane, 4,4'-(1,3-adamantanediyl)diphenol and 1,3-bis(4-hydroxyphenyl)-5,7-dimethyladamantane.

Out of these, 1,1-bis(4-hydroxyphenyl)-1-phenylethane, 2,2-bis(4-hydroxyphenyl)propane, 2,2-bis(4-hydroxy-3-methylphenyl)propane, 1,1-bis(4-hydroxyphenyl)cyclohexane, 1,1-bis(4-hydroxyphenyl)-3,3,5-trimethylcyclohexane, 4,4'-sulfonyldiphenol, 2,2'-dimethyl-4,4'-sulfonyldiphenol, 9,9-bis(4-hydroxy-3-methylphenyl) fluorene, 1,3-bis{2-(4-hydroxyphenyl)propyl}benzene and 1,4-bis{2-(4-hydroxyphenyl)propyl}benzene are preferred. 2,2-bis(4-hydroxyphenyl)propane, 1,1-bis(4-hydroxyphenyl)cyclohexane (BPZ), 4,4'-sulfonyldiphenol and 9,9-bis (4-hydroxy-3-methylphenyl)fluorene are particularly preferred. 2,2-bis(4-hydroxyphenyl)propane, which has excellent strength and high durability is most preferred. They may be used alone or in combination of two or more.

As the hydroxyaryl-terminated polydiorganosiloxane represented by the above general formula (3), the following compounds are preferably used.

[Chem 4]

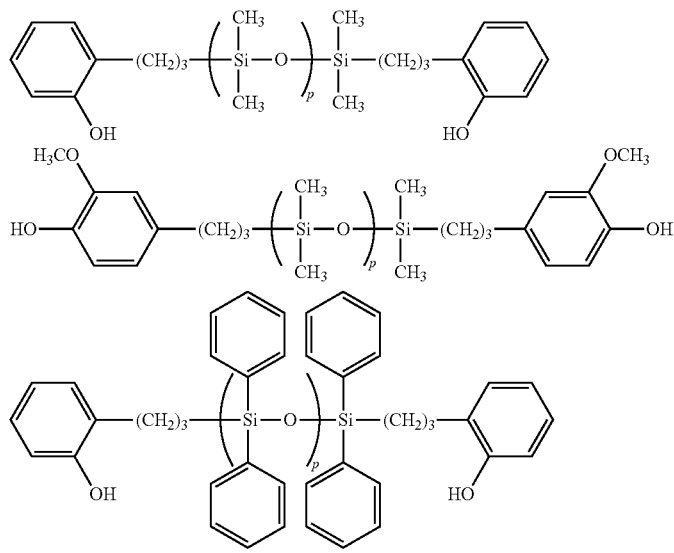

-continued

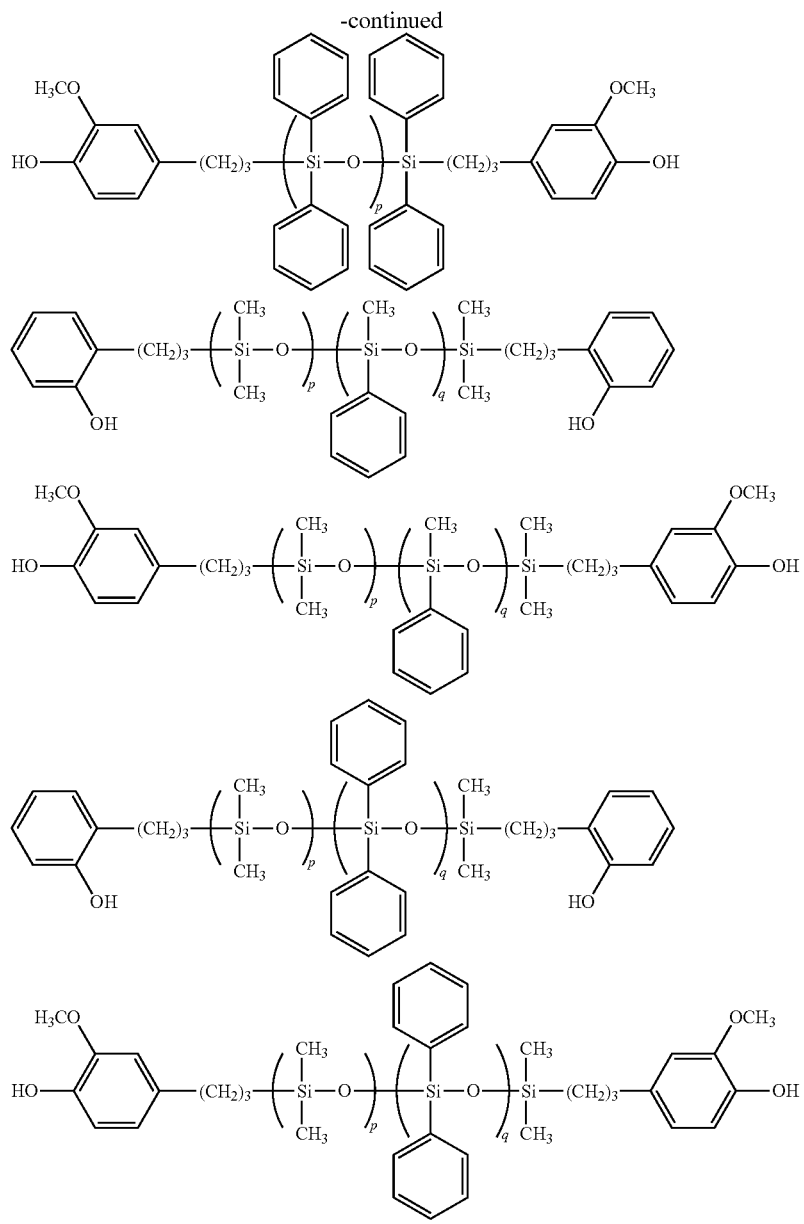

The hydroxyaryl-terminated polydiorganosiloxane (II) is easily produced by hydrosilylating a phenol having an olefinic unsaturated carbon-carbon bond, preferably vinyl phenol, 2-allylphenol, isopropenyl phenol or 2-methoxy-4-allylphenol to the end of a polysiloxane chain having a predetermined polymerization degree. (2-allylphenol)-terminated polydiorganosiloxanes and (2-methoxy-4-allylphenol)-terminated polydiorganosiloxanes are preferred, and (2-allylphenol)-terminated polydimethylsiloxane and (2-methoxy-4-allylphenol)-terminated polydimethylsiloxane are particularly preferred. The molecular weight distribution (Mw/Mn) of the hydroxyaryl-terminated polydiorganosiloxane (II) is preferably not more than 3. To develop more excellent low-outgas properties at the time of high-temperature molding and low-temperature impact resistance, the molecular weight distribution (Mw/Mn) is more preferably not more than 2.5, much more preferably not more than 2. When the molecular weight distribution exceeds the upper limit of the above preferred range, the amount of a gas generated at the time of high-temperature molding becomes large and low-temperature impact resistance may deteriorate.

The diorganosiloxane polymerization degree (p+q) of the hydroxyaryl-terminated polydiorganosiloxane (II) is suitably 10 to 300 to obtain high impact resistance. The diorganosiloxane polymerization degree (p+q) is preferably 10 to 200, more preferably 12 to 150, much more preferably 14 to 100. Below the lower limit of the above preferred range, impact resistance which is the characteristic property of the polycarbonate-polydiorganosiloxane copolymer is not effectively developed, and above the upper limit of the above preferred range, a poor appearance is obtained.

The content of the polydiorganosiloxane is preferably 0.1 to 50 wt % based on the total weight of the polycarbonate-polydiorganosiloxane copolymer resin used in the component A. The content of the polydiorganosiloxane component is more preferably 0.5 to 30 wt %, much more preferably 1 to 20 wt %. At or above the lower limit of the above preferred range, impact resistance and flame retardancy become excellent, and at or below the upper limit of the above preferred range, a stable appearance which is hardly affected by molding conditions is readily obtained. The polymerization degree of the polydiorganosiloxane and the content of the polydiorganosiloxane can be calculated by 1H-NMR measurement.

In the present invention, hydroxyaryl-terminated polydiorganosiloxanes (II) may be used alone or in combination of two or more.

As long as the present invention is not impeded, other comonomer except for the dihydric phenol (I) and the hydroxyaryl-terminated polydiorganosiloxane (II) may be used in an amount of not more than 10 wt % based on the total weight of the copolymer.

In the present invention, a mixed solution containing an oligomer having a terminal chloroformate group is prepared through a reaction between the dihydric phenol (I) and a carbonate ester forming compound in a mixed solution of a water-insoluble organic solvent and an alkali aqueous solution in advance.

To produce the oligomer of the dihydric phenol (I), the whole amount of the dihydric phenol (I) in use may be changed to the oligomer at a time, or part thereof as a post-addition monomer may be added as a reaction raw material in a post-stage of an interfacial polycondensation reaction. The term "post-addition monomer" means that a monomer is added to accelerate the post-stage of the polycondensation reaction, and does not need to be added when not required.

This oligomer production reaction system is not particularly limited but preferably system in which the reaction is carried out in a solvent in the presence of an acid binder.

The amount of the carbonate ester forming compound may be suitably adjusted in consideration of the stoichiometric ratio (equivalent) of the reaction. When a gaseous carbonate ester forming compound such as phosgene is used, it is preferably blown into the reaction system.

As the acid binder may be used an alkali metal hydroxide such as sodium hydroxide or potassium hydroxide, an alkali metal carbonate such as sodium carbonate or potassium carbonate, an organic base such as pyridine, or a mixture thereof. The amount of the acid binder may be suitably determined in consideration of the stoichiometric ratio (equivalent) of the reaction likewise. Stated more specifically, 2 equivalents or a little more than that of the acid binder is preferably used based on the number of moles (1 mole is generally equivalent to 2 equivalents) of the dihydric phenol (I) used for the formation of the oligomer.

As the solvent, solvents which are inactive to reactions such as known solvents used to produce polycarbonates may be used alone or as a mixture. Typical examples of the solvent include hydrocarbon solvents such as xylene and halogenated hydrocarbon solvents such as methylene chloride and chlorobenzene. Halogenated hydrocarbon solvents such as methylene chloride are particularly preferably used.

Although the reaction pressure for producing the oligomer is not particularly limited and may be normal pressure, increased pressure or reduced pressure, the reaction is advantageously carried out under normal pressure. The reaction temperature is selected from a range of −20 to 50° C., and water cooling or ice cooling is desirably carried out as heat is generated by polymerization in most cases. Although the reaction time is affected by other conditions and cannot be specified unconditionally, it is generally 0.2 to 10 hours. The pH range of the oligomer production reaction is the same as that of a known interfacial reaction and always adjusted to not less than 10.

Thus, in the present invention, the polycarbonate-polydiorganosiloxane copolymer is obtained by obtaining a mixed solution containing the oligomer of the dihydric phenol (I) having a terminal chloroformate group, adding the highly purified hydroxyaryl-terminated polydiorganosiloxane (II) represented by the general formula (4) having a molecular weight distribution (Mw/Mn) of not more than 3 while the mixed solution is stirred, and carrying out the interfacial polycondensation of the hydroxyaryl-terminated polydiorganosiloxane (II) and the oligomer.

[Chem 5]

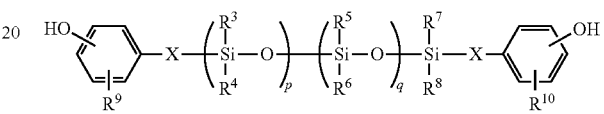

(4)

(In the above formula (4), $R^3$, $R^4$, $R^5$, $R^6$, $R^7$ and $R^8$ are each independently a hydrogen atom, alkyl group having 1 to 12 carbon atoms, or substituted or nonsubstituted aryl group having 6 to 12 carbon atoms, $R^9$ and $R^{10}$ are each independently a hydrogen atom, halogen atom, alkyl group having 1 to 10 carbon atoms, or alkoxy group having 1 to 10 carbon atoms, "p" is a natural number, "q" is 0 or a natural number and (p+q) is a natural number of 10 to 300. X is a divalent aliphatic group having 2 to 8 carbon atoms.)

For the interfacial polycondensation reaction, an acid binder may be suitably added in consideration of the stoichiometric ratio (equivalent) of the reaction. As the acid binder, for example, an alkali metal hydroxide such as sodium hydroxide or potassium hydroxide, an alkali metal carbonate such as sodium carbonate or potassium carbonate, an organic base such as pyridine, or a mixture thereof may be used. Stated more specifically, when the hydroxyaryl-terminated polydiorganosiloxane (II) in use or part of the dihydric phenol (1) as a post-addition monomer is added in this reaction stage, 2 equivalents or more than that of an alkali is preferably used based on the total number of moles (1 mole is generally equivalent to 2 equivalents) of the post-addition dihydric phenol (I) and the hydroxyaryl-terminated polydiorganosiloxane (II).

Polycondensation by an interfacial polycondensation reaction between the oligomer of the dihydric phenol (I) and the hydroxyaryl-terminated polydiorganosiloxane (II) is carried out by stirring the above mixed solution violently.

In the polycondensation reaction, an end sealing agent or a molecular weight control agent is generally used. Examples of the end sealing agent include compounds having a monovalent phenolic hydroxyl group such as ordinary phenol, p-tert-butylphenol, p-cumylphenol and tribromophenol, long-chain alkyl phenols, aliphatic carboxylic acid chlorides, aliphatic carboxylic acids, hydroxybenzoic acid alkyl esters, hydroxyphenyl alkyl acid esters and alkyl ether phenols. The amount of the end sealing agent is 100 to 0.5 mole, preferably 50 to 2 moles based on 100 moles of the total of all the dihydric phenol-based compounds. Two or more of the above compounds may be used in combination as a matter of course.

To promote the polycondensation reaction, a catalyst such as a tertiary amine exemplified by triethylamine or a quaternary ammonium salt may be added.

The reaction time of the polycondensation reaction is preferably not less than 30 minutes, more preferably not less than 50 minutes. A small amount of an antioxidant such as sodium sulfide or hydrosulfide may be added as desired.

A branching agent may be used in combination with the above dihydric phenol-based compound to obtain a branched polycarbonate-polydiorganosiloxane. Examples of the polyfunctional aromatic compound having 3 or more functional groups used for the branched polycarbonate-polydiorganosiloxane copolymer resin include phloroglucin, phloroglucide and 4,6-dimethyl-2,4,6-tris(4-hydroxydiphenyl)heptene-2, 2,4,6-trimethyl-2,4,6-tris(4-hydroxyphenyl) heptane, 1,3,5-tris(4-hydroxyphenyl)benzene, 1,1,1-tris(4-hydroxyphenyl)ethane, 1,1,1-tris(3,5-dimethyl-4-hydroxyphenyl)ethane, 2,6-bis(2-hydroxy-5-methylbenzyl)-4-methylphenol and 4-{4-[1,1-bis(4-hydroxyphenyl)ethyl]benzene}-α,α-dimethylbenzyl phenol and other trisphenols, tetra(4-hydroxyphenyl)methane, bis(2,4-dihydroxyphenyl) ketone and 1,4-bis(4,4-dihydroxytriphenylmethyl)benzene, trimellitic acid, pyromellitic acid, benzophenonetetracarboxylic acid and acid chlorides thereof. Out of these, 1,1,1-tris(4-hydroxyphenyl)ethane and 1,1,1-tris(3,5-dimethyl-4-hydroxyphenyl)ethane are preferred, and 1,1,1-tris(4-hydroxyphenyl)ethane is particularly preferred. The amount of the polyfunctional compound in the branched polycarbonate-polydiorganosiloxane copolymer resin is preferably 0.001 to 1 mol %, more preferably 0.005 to 0.9 mol %, much more preferably 0.01 to 0.8 mol %, particularly preferably 0.05 to 0.4 mol % based on the whole amount of the aromatic polycarbonate-polydiorganosiloxane copolymer resin. The amount of the branched structure can be calculated by 1H-NMR measurement.

The reaction pressure may be reduced pressure, normal pressure or increased pressure but preferably normal pressure or the pressure of reaction system itself. The reaction temperature is selected from a range of −20 to 50° C., and water cooling or ice cooling is desirably carried out as heat is generated by polymerization in most cases. Since the reaction time differs according to other conditions such as the reaction temperature, it cannot be specified unconditionally but generally 0.5 to 10 hours.

According to circumstances, a polycarbonate-polydiorganosiloxane copolymer resin having a desired reduced viscosity [$\eta_{sp}/C$] may be acquired by carrying out a suitable physical treatment (mixing, fractionating) and/or chemical treatment (polymer reaction, crosslinking, partial decomposition) on the obtained polycarbonate-polydiorganosiloxane copolymer resin.

The obtained reaction product (crude product) is subjected to a known post-treatment such as separation and purification to collect a polycarbonate-polydiorganosiloxane copolymer resin having a desired purity (degree of purification). The average size of polydiorganosiloxane domains in a molded article of the polycarbonate-polydiorganosiloxane copolymer resin is preferably 1 to 40 nm. The average size is more preferably 1 to 30 nm, much more preferably 5 to 25 nm. Below the lower limit of the preferred range, impact resistance and flame retardancy are not fully developed, and above the upper limit of the preferred range, impact resistance may not be developed stably. Thereby, a polycarbonate resin composition which is excellent in impact resistance and appearance is provided.

For the present invention, the average domain size of the polydiorganosiloxane domains in a molded article of the polycarbonate-polydiorganosiloxane copolymer resin was evaluated by a small-angle X-ray scattering (SAXS) method. The small-angle X-ray scattering method is a method for measuring diffuse scattering and diffraction produced in a small-angle area having a scattering angle (2θ) of less than 10°. In this small-angle X-ray scattering method, when there are areas having a difference of about 1 to 100 nm in electron density in a substance, the diffuse scattering of X-rays is measured due to the electron density difference. The particle diameter of an object to be measured is obtained based on this scattering angle and scattering intensity. In the case of a polycarbonate-polydiorganosiloxane copolymer resin having an aggregation structure in which polydiorganosiloxane domains are dispersed in the matrix of a polycarbonate polymer, the diffuse scattering of X-rays occurs due to a difference in electron density between the polycarbonate matrix and the polydiorganosiloxane domains. A small-angle X-ray scattering profile is measured by measuring scattering intensity I at each scattering angle (2θ) of less than 10°, and simulation is carried out from temporary particle diameter and temporary particle size distribution models by using commercially available analyzing software based on the assumption that the polydiorganosiloxane domains are spherical domains and there are variations in particle size distribution so as to obtain the average size of the polydiorganosiloxane domains. According to the small-angle X-ray scattering method, the average size of the polydiorganosiloxane domains dispersed in the matrix of the polycarbonate polymer which cannot be accurately measured by observation through a transmission electron microscope can be measured easily and accurately with high reproducibility. The term "average domain size" means the number average of individual domain sizes.

The terms "average domain size" in the context of the present invention is a measurement value obtained by measuring a 1.0 mm-thick part of a three-stage plate, which is manufactured according to the method described in the Example section, by the small-angle X-ray scattering method. Analysis was conducted with isolated particle models which do not take interaction between particles (interference between particles) into consideration.

<Component B: Polyolefin-Based Resin>

The resin composition of the present invention comprises a polyolefin-based resin as component B. The polyolefin-based resin is a synthetic resin obtained by polymerizing or copolymerizing an olefin-based monomer having a radically polymerizable double bond. The olefin-based monomers are not limited but include α-olefins such as ethylene, propylene, 1-butene, 1-pentene, 1-hexene, 1-heptene, 1-octene and 4-methyl-1-pentene, and conjugated dienes such as butadiene and isoprene. The olefin-based monomers may be used alone or in combination of two or more. Polyolefin-based resins are not limited but include for example polymer of ethylene, copolymer of ethylene and α-olefin other than ethylene, polymer of propylene, copolymer of propylene and α-olefin other than propylene, polymer of butene, or polymer or copolymer of conjugated dienes such as butadiene and isoprene. Preferable examples include polymer of propylene, copolymer of propylene and α-olefin other than propylene. Polymer of propylene is more preferable. Polyolefin-based resin may be used alone or in combination of two ore more.

From the viewpoints of versatility and stiffness, a polypropylene-based resin is more preferably used in the present invention. Although the polypropylene-based resin is a propylene polymer, in the present invention, it includes a copolymer of propylene and another monomer. Examples of the polypropylene-based resin in the present invention include homopolypropylene resins, block copolymers of propylene, ethylene and an α-olefin having 4 to 10 carbon atoms (may also be called "block polypropylene"), and random copolymers of propylene, ethylene and an α-olefin having 4 to 10 carbon atoms (may also be called "random polypropylene"). The block polypropylenes and the random polypropylenes are also collectively called "polypropylene copolymers".

In the present invention, the above homopolypropylene resins, the block polypropylenes and the random polypropylenes may be used alone or in combination of two or more as the polypropylene-based resin, and the homopolypropylenes and the block polypropylenes are preferred.

Examples of the α-olefin having 4 to 10 carbon atoms used in the polypropylene copolymers include 1-butene, 1-pentene, isobutylene, 3-methyl-1-butene, 1-hexene, 3,4-dimethyl-1-butene, 1-heptene and 3-methyl-1-hexene.

The content of ethylene in the polypropylene copolymer is preferably not more than 5 mass % based on the total of all the monomers. The content of the α-olefin having 4 to 10 carbon atoms in the polypropylene copolymer is preferably not more than 20 mass % based on the total of all the monomers.

The polypropylene copolymer is preferably a copolymer of propylene and ethylene, or a copolymer of propylene and 1-butene, particularly preferably a copolymer of propylene and ethylene.

The melt flow rate (230° C., 2.16 kg) of the polyolefin-based resin of the present invention is preferably 0.1 to 10 g/10 min, more preferably 0.3 to 5 g/10 min, much more preferably 0.5 to 3 g/10 min. When the melt flow rate of the polypropylene-based resin is within this range, fluidity and mechanical properties are preferable. The melt flow rate is also called "MFR". MFR is measured in accordance with ISO1133.

In the present invention, a modified polyolefin-based resin may be used alone as the polyolefin-based resin. Alternatively, the polyolefin-based resin may be used in combination with the modified polyolefin-based resin. The modified polyolefin resin is a polyolefin-based resin which is modified and has a polar group. The polar group to be modified is at least one functional group selected from the group consisting of acidic groups such as epoxy group, glycidyl group and carboxyl group, and acid derivatives such as acid anhydride groups. More specifically, a polyolefin-based resin obtained by copolymerizing a monomer having a polar group such as epoxy group, carboxyl group or acid anhydride group with the above polyolefin-based resin may be preferably used. Further, a graft copolymerized polyolefin-based resin may be more preferably used. Preferred examples of the monomer having an epoxy group include glycidyl methacrylate, butyl glycidyl maleate, butyl glycidyl fumarate, propyl glycidyl fumarate, glycidyl acrylate and N-(4-(2,3-epoxy)-3,5-dimethyl)acrylamide. Examples of the monomer having a carboxyl group include acrylic acid, methacrylic acid and maleic acid. Examples of the monomer containing an acid anhydride include maleic anhydride, itaconic anhydride and citraconic anhydride. Out of the above monomers having a polar group, acrylic acid and maleic anhydride are preferred from the viewpoints of reactivity and acquisition ease.

The content of the component B is preferably 5 to 50 parts by weight, more preferably 10 to 45 parts by weight, much more preferably 15 to 40 parts by weight based on 100 parts by weight of the total of the components A and B. When the content is within the above range, preferable chemical resistance, mechanical properties, and heat resistance are obtained.

<Component C: Styrene-Based Thermoplastic Elastomor>

The resin composition of the present invention comprises styrene-based thermoplastic elastomer as the component C. The stylene-based thermoplastic elastomer used in the present invention is preferably block co-polymer represented by the following formula (I) or (II).

X in the general formula (I) and (II) is an aromatic vinyl polymer block, the polymerization degree may be the same or may be different at both ends of the molecular chain in equation (I). Further, Y is selected at least one from the group consisting of butadiene polymer block, isoprene polymer block, butadiene/isoprene copolymer block, hydrogenated butadiene polymer block, hydrogenated isoprene polymer block, hydrogenated butadiene/isoprene copolymer block, partially hydrogenated butadiene polymer block, the partially hydrogenated isoprene polymer block and partially hydrogenated butadiene/isoprene copolymer block. Further, n is an integer of 1 or more.

Specific examples include styrene-ethylene.butylene-styrene copolymer, styrene-ethylene.propylene-styrene copolymer, styrene-ethylene.ethylene.propylene-styrene copolymer, styrene-butadiene-butene-styrene copolymer, styrene-butadiene-styrene copolymer, styrene-isoprene-styrene copolymer, styrene-hydrogenated butadiene di-block copolymer, styrene-hydrogenated isoprene di-block copolymer, styrene-butadien di-block copolymer, styrene-isoprane di-block copolymers and the like. Among them, styrene-ethylene.butylene-styrene copolymer, styrene-ethylene.propylene-styrene copolymer, styrene-ethylene.ethylene.propylene-styrene copolymer, styrene-butadiene-butene-styrene copolymer is the most preferred.

The content of component X in the above block copolymer is 40 to 80 wt %, more preferably 45 to 75 wt %, much more preferably 50 to 70 wt %. When this content is suitable, preferable compatibility between the component A and B as well as mechanical properties and chemical resistance of the resin component are obtained.

The weight average molecular weight of the styrene-based thermoplastic elastomer is preferably not more than 250,000, more preferably not more than 200,000, much more preferably not more than 150,000. When the weight average molecular weight is within this range, desirable moldability and dispersibility in the resin composition are obtained. The lower limit of the weight average molecular weight is not particularly limited but preferably not less than 40,000, more preferably not less than 50,000. The weight average molecular weight was measured by the following method. That is, the weight average molecular weight was calculated by measuring molecular weight in terms of polystyrene by gel permeation chromatography. The melt flow rate (230° C., 2.16 kg) of the styrene-based thermoplastic elastomer is preferably 0.1 to 10 g/10 min, more preferably 0.15 to 9 g/10 min, particularly preferably 0.2 to 8 g/10 min. When the melt flow rate of the styrene-based thermoplastic elastomer is within the preferable range, satisfactory toughness is obtained. Note that MFR is measured in accordance with ISO 1133 at 230° C. under a load of 2.16 kg. Furthermore, the ratio of the melt flow rates (230° C., 2.16 kg) of component B and component C (MFR of component B/MFR of component C) is preferably 0.5 to 10, more preferably 0.8 to 9, and further preferably 1 to 8. As long as this ratio is appropriate, preferable compatibility between the resins and preferable mechanical properties are obtained.

The content of the component C is 1 to 30 parts by weight, preferably 3 to 28 parts by weight, more preferably 5 to 25 parts by weight based on 100 parts by weight of the total of the components A and B. When the content of the component C is appropriate, mechanical properties, chemical resistance, and heat resistance are suitable.

In the present invention, stylene-based elastomer of the component C may also be modified as in the case of the component B.

<Component D: Core-Shell Type Graft Polymer>

The resin composition of the present invention may comprise a core-shell type graft polymer as the component D. The core-shell type graft polymer is a graft copolymer obtained by copolymerizing a rubber component having a glass transition temperature of 10° C. or lower as a core and one or more monomers selected from aromatic vinyl, vinyl cyanide, acrylic acid ester, methacrylic acid ester and vinyl compound copolymerizable with these as a shell.

Examples of the rubber component of the component D include butadiene rubber, butadiene-acrylic composite rubber, acrylic rubber, acrylic-silicone composite rubber, isobutylene-silicone composite rubber, isoprene rubber, styrene-butadiene rubber, chloroprene rubber, ethylene-propylene rubber, nitrile rubber, ethylene-acrylic rubber, silicone rubber, epichlorohydrin rubber, fluorine rubber and rubbers obtained by adding hydrogen to the unsaturated bonds of these rubbers. A rubber component containing no halogen atom is preferred from the viewpoint of an environmental load due to anxiety about the generation of a harmful substance at the time of combustion. The glass transition temperature of the rubber component is preferably −10° C. or lower, more preferably −30° C. or lower. The rubber component is preferably butadiene rubber, butadiene-acrylic composite rubber, acrylic rubber or acrylic-silicone composite rubber. The composite rubber is a rubber obtained by copolymerizing two different rubber components or a polymerized rubber having an IPN structure in which two different rubber components are intertwined with each other such that they cannot be separated from each other. The weight average particle diameter of the core in the core-shell type graft polymer is preferably 0.05 to 0.8 more preferably 0.1 to 0.6 μm, much more preferably 0.15 to 0.5 μm. When the particle diameter is in the range of 0.05 to 0.8 μm, better impact resistance is obtained.

Examples of the aromatic vinyl in the vinyl compound to be copolymerized as the shell of the core-shell type graft polymer with the rubber component include styrene, α-methylstyrene, p-methylstyrene, alkoxystyrene and halogenated styrene. Examples of the acrylic acid ester include methyl acrylate, ethyl acrylate, butyl acrylate, cyclohexyl acrylate and octyl acrylate. Examples of the methacrylic acid ester include methyl methacrylate, ethyl methacrylate, butyl methacrylate, cyclohexyl methacrylate and octyl methacrylate. Out of these, methyl methacrylate is particularly preferred. Preferably, the core-shell type graft polymer comprises a methacrylic acid ester such as methyl methacrylate as an essential component. This is because the core-shell type graft polymer has excellent affinity for the aromatic polycarbonate resin, whereby a large amount of the rubber component is existent in the aromatic polycarbonate resin, and the high impact resistance of the aromatic polycarbonate resin is developed more effectively with the result that the impact resistance of the resin composition becomes high. Stated more specifically, the methacrylic acid ester is contained in an amount of not less than 10 wt %, more preferably not less than 15 wt % based on 100 wt % of the graft component (100 wt % of the shell, in the case of core-shell type polymer). An elastic polymer containing a rubber component having a glass transition temperature of 10° C. or lower may be produced by bulk polymerization, solution polymerization, suspension polymerization or emulsion polymerization, and the copolymerization system may be one-stage graft or multi-stage graft copolymerization. It may be a mixture with a copolymer comprising only a graft component by-produced at the time of manufacture. Further, a soap-free polymerization method using an initiator such as potassium persulfate, seed polymerization method or two-stage swelling polymerization method may also be used besides the general emulsion polymerization method. In the suspension polymerization method, a water phase and a monomer phase may be separately kept and supplied into a continuous disperser accurately in order to control the particle size by the revolution of the disperser. In the continuous production method, the particle size may be controlled by supplying a monomer phase into an aqueous solution having dispersion ability through a fine orifice or porous filter having an opening size of several to several tens of μm. In the case of the core-shell type graft polymer, the reaction may be carried out in a single stage or multiple stages for both of the core and the shell.

The polymer is commercially available and can be easily acquired. Polymers comprising butadiene rubber as the main rubber component include the Kane Ace M series (for example, M-711 comprising methyl methacrylate as the main shell component, M-701 comprising methyl methacrylate styrene as the main shell component) of Kaneka Corporation, the METABLEN C series (for example, C-223A comprising methyl methacrylate styrene as the main shell component) and E series (for example, E-870A comprising methyl methacrylate styrene as the main shell component) of Mitsubishi Rayon Co., Ltd. and the PARALOID EXL series (for example, EXL-2690 comprising methyl methacrylate as the main shell component) of Dow Chemical Company. Polymers comprising acrylic rubber or butadiene-acrylic composite rubber as the main rubber component include W series (for example, W-600A comprising methyl methacrylate as the main shell component) and the PARALOID EXL series (for example, EXL-2390 comprising methyl methacrylate as the main shell component) of DOW Chemical Company. Polymers comprising acrylic-silicone composite rubber as the main rubber component include METABLEN S-2501 comprising methyl methacrylate as the main shell component and SX-200R comprising acrylonitrile styrene as the main shell component from Mitsubishi Rayon Co., Ltd.

The content of the component D is preferably 1 to 10 parts by weight, more preferably 1 to 8 parts by weight, much more preferably 2 to 7 parts by weight based on 100 parts by weight of the total of the components A and B. Although mechanical properties and chemical resistance are further improved by adding the component D, these effects do not develop when the content is less than 1 parts by weight. When the content is higher than 10 parts by weight, heat resistance may degrade.

<Other Additives>

(i) Phosphorus-Based Stabilizer

Examples of the phosphorus-based stabilizer include phosphorous acid, phosphoric acid, phosphonous acid, phosphonic acid and esters thereof, and a tertiary phosphine.

Examples of the phosphite compound include triphenyl phosphite, tris(nonylphenyl)phosphite, tridecyl phosphite, trioctyl phosphite, trioctadecyl phosphite, didecylmonophenyl phosphite, dioctylmonophenyl phosphite, diisopropylmonophenyl phosphite, monobutyldiphenyl phosphite, monodecyldiphenyl phosphite, monooctyldiphenyl phosphite, tris(diethylphenyl)phosphite, tris(di-iso-propylphenyl)phosphite, tris(di-n-butylphenyl)phosphite, tris(2,4-di-tert-butylphenyl)phosphite, tris(2,6-di-tert-butylphenyl) phosphite, di stearyl pentaerythritol diphosphite, bis(2,4-di-tert-butylphenyl)pentaerythritol diphosphite, bis(2,6-tert-butyl-4-methylphenyl)pentaerythritol diphosphite, bis(2,6-di-tert-butyl-4-ethylphenyl)pentaerythritol diphosphite, bis{2,4-bis(1-methyl-1-phenylethyl)phenyl} pentaerythritol diphosphite, phenyl bisphenol A pentaerythritol diphosphite, bis(nonylphenyl)pentaerythritol diphosphite and dicyclohexyl pentaerythritol diphosphite.

Other phosphite compounds which react with a dihydric phenol and have a cyclic structure may also be used. The phosphite compounds include 2,2'-methylenebis(4,6-di-tert-butylphenyl)(2,4-di-tert-butylphenyl)phosphite, 2,2'-methylenebis(4,6-di-tert-butylphenyl) (2-tert-butyl-4-methylphenyl)phosphite and 2,2'-methylenebis(4,6-di-tert-butylphenyl)octyl phosphite.

Examples of the phosphate compound include tributyl phosphate, trimethyl phosphate, tricresyl phosphate, triphenyl phosphate, trichlorophenyl phosphate, triethyl phosphate, diphenylcresyl phosphate, diphenylmonoorthoxenyl phosphate, tributoxyethyl phosphate, dibutyl phosphate, dioctyl phosphate and diisopropyl phosphate. Triphenyl phosphate and trimethyl phosphate are preferred.

Examples of the phosphonite compound include tetrakis(2,4-di-tert-butylphenyl)-4,4'-biphenylene diphosphonite, tetrakis(2,4-di-tert-butylphenyl)-4,3'-biphenylene diphosphonite, tetrakis(2,4-di-tert-butylphenyl)-3,3'-biphenylene diphosphonite, tetrakis(2,6-di-tert-butylphenyl)-4,4'-biphenylene diphosphonite, tetrakis(2,6-di-tert-butylphenyl)-4,3'-biphenylene diphosphonite, tetrakis(2,6-di-tert-butylphenyl)-3,3'-biphenylene diphosphonite, bis(2,4-di-tert-butylphenyl)-4-phenyl-phenyl phosphonite, bis(2,4-di-tert-butylphenyl)-3-phenyl-phenyl phosphonite, bis(2,6-di-n-butylphenyl)-3-phenyl-phenyl phosphonite, bis(2,6-di-tert-butylphenyl)-4-phenyl-phenyl phosphonite and bis(2,6-di-tert-butylphenyl)-3-phenyl-phenyl phosphonite. Tetrakis(di-tert-butylphenyl)-biphenylene diphosphonites and bis(di-tert-butylphenyl)-phenyl-phenyl phosphonites are preferred, and tetrakis(2,4-di-tert-butylphenyl)-biphenylene diphosphonites and bis(2,4-di-tert-butylphenyl)-phenyl-phenyl phosphonites are more preferred. The phosphonite compound may be and is preferably used in combination with the above phosphite compound having an aryl group substituted to the two or more alkyl groups.

Examples of the phosphonate compound include dimethyl benzenephosphonate, diethyl benzenephosphonate and dipropyl benzenephosphonate.

Examples of the tertiary phosphine include triethylphosphine, tripropylphosphine, tributylphosphine, trioctylphosphine, triamylphosphine, dimethylphenylphosphine, dibutylphenylphosphine, diphenylmethylphosphine, diphenyloctylphosphine, triphenylphosphine, tri-p-tolylphosphine, trinaphthylphosphine and diphenylbenzylphosphine. Triphenylphosphine is particularly preferred as the tertiary phosphine.

The above phosphorus-based stabilizers may be used alone or in combination of two or more. Out of these phosphorus-based stabilizers, phosphonite compounds or phosphite compounds represented by the following general formula (5) are preferred.

[Chem 6]

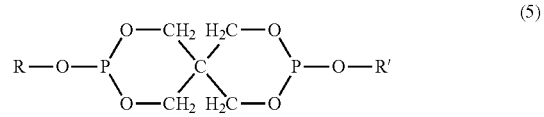

(5)

(In the formula (5), R and R' are each an alkyl group having 6 to 30 carbon atoms or aryl group having 6 to 30 carbon atoms and may be the same or different.)

As described above, tetrakis(2,4-di-tert-butylphenyl)-biphenylene diphosphonites are preferred as the phosphonite compound. Stabilizers comprising this phosphonite as the main component are marketed under the trade names of Sandostab P-EPQ (trademark, manufactured by Clariant) and Irgafos P-EPQ (trademark, manufactured by CIBA SPECIALTY CHEMICALS) and may all be used.

More preferred phosphite compounds of the above formula (5) are distearyl pentaerythritol diphosphite, bis(2,4-di-tert-butylphenyl)pentaerythritol diphosphite, bis(2,6-di-tert-butyl-4-methylphenyl)pentaerythritol diphosphite and bis{2,4-bis(1-methyl-1-phenylethyl)phenyl}pentaerythritol diphosphite.

Distearyl pentaerythritol diphosphite is marketed under the trade names of ADK STAB PEP-8 (trademark, manufactured by ADEKA Corporation) and JPP681S (trademark, manufactured by Johoku Chemical Engineering Co., Ltd.), and may all be used. Bis(2,4-di-tert-butylphenyl)pentaerythritol diphosphite is marketed under the trade names of ADK STAB PEP-24G (trademark, manufactured by ADEKA Corporation), Al kanox P-24 (trademark, manufactured by Great Lakes Corporation), Ultranox P626 (trademark, manufactured by GE Specialty Chemicals), Doverphos S-9432 (trademark, manufactured by Dover Chemical Corporation) and Irgafos 126 and 126FF (trademarks, manufactured by CIBA SPECIALTY CHEMICALS), and may all be used. Bis(2,6-di-tert-butyl-4-methylphenyl)pentaerythritol diphosphite is marketed under the trade name of ADK STAB PEP-36 (trademark, manufactured by ADEKA Corporation) and may be easily used. Bis{2,4-bis(1-methyl-1-phenylethyl)phenyl}pentaerythritol diphosphite is marketed under the trade names of ADK STAB PEP-45 (trademark, manufactured by ADEKA Corporation) and Doverphos S-9228 (trademark, manufactured by Dover Chemical Corporation), and may all be used.

The above phosphorus-based stabilizes may be used alone or in combination of two or more. The content of the phosphorus-based stabilizer is preferably 0.01 to 1.0 part by weight, more preferably 0.03 to 0.8 part by weight, much more preferably 0.05 to 0.5 part by weight based on 100 parts by weight of the total of the components A and B. When the content is lower than 0.01 part by weight, a thermal decomposition control effect is not obtained at the time of processing and mechanical properties may not deteriorate, and even when the content is higher than 1.0 part by weight, mechanical properties may deteriorate.

(ii) Phenol-Based Stabilizer

The resin composition of the present invention may comprise a phenol-based stabilizer. The phenol-based stabilizer is generally a hindered phenol, semi-hindered phenol or less-hindered phenol compound. A hindered phenol compound is preferably used as it thermally stabilizes a polypropylene-based resin. Examples of the hindered phenol compound include α-tocopherol, butylhydroxytoluene, sinapyl alcohol, vitamin E, octadecyl-3-(3,5-di-tert-butyl-4-hydroxyphenyl) propionate, 2-tert-butyl-6-(3'-tert-butyl-5'-methyl-2'-hydroxybenzyl)-4-methylphenyl acrylate, 2,6-di-tert-butyl-4-(N,N-dimethylaminomethyl)phenol, 3,5-di-tert-butyl-4-hydroxybenzylphosphonate diethyl ester, 2,2'-methylenebis(4-methyl-6-tert-butylphenol), 2,2'-methylenebis(4-ethyl-6-tert-butylphenol), 4,4'-methylenebis(2,6-di-tert-butylphenol), 2,2'-methylenebis(4-methyl-6-cyclohexylphenol), 2,2'-dimethylene-bis(6-α-methyl-benzyl-p-cresol), 2,2'-ethylidene-bis(4,6-di-tert-butylphenol), 2,2'-butylidene-bis(4-methyl-6-tert-butylphenol), 4,4'-butylidene-bis(3-methyl-6-tert-butylphenol), triethylene glycol-N-bis-3-(3-tert-butyl-4-hydroxy-5-methylphenyl) propionate, 1,6-hexanediol-bis[3-(3,5-di-tert-butyl-4-hydroxyphenyl) propionate], bis[2-tert-butyl-4-methyl-6-(3-tert-butyl-5-methyl-2-hydroxybenzyl) phenyl]terephthalate, 3,9-bis{2-[3-(3-tert-butyl-4-hydroxy-5-methylphenyl) propionyloxy]-1,1-dimethylethyl}-2,4,8,10-tetraoxaspiro [5,5]undecane, 4,4'-thiobis(6-tert-butyl-m-cresol), 4,4'-thiobis(3-methyl-6-tert-butylphenol), 2,2'-thiobis(4-methyl-6-tert-butylphenol), bis(3,5-di-tert-butyl-4-hydroxybenzyl)sulfide, 4,4'-di-thiobis(2,6-di-tert-butylphenol), 4,4'-tri-thiobis(2,6-di-tert-butylphenol), 2,2-thiodiethylenebis-[3-(3,5-di-tert-butyl-4-hydroxyphenyl) propionate], 2,4-bis(n-octylthio)-6-(4-hydroxy-3,5-di-tert-butylanilino)-1,3,5-triazine, N,N'-hexamethylenebis-(3,5-di-tert-butyl-4-hydroxyhydrocinnamide), N,N'-bis[3-(3,5-di-tert-butyl-4-hydroxyphenyl)propionyl] hydrazine, 1,1,3-tris(2-methyl-4-hydroxy-5-tert-butylphenyl)butane, 1,3,5-trimethyl-2,4,6-tris(3,5-di-tert-butyl-4-hydroxybenzyl) benzene, tris(3,5-di-tert-butyl-4-hydroxyphenyl)isocyanurate, tris(3,5-di-tert-butyl-4-hydroxybenzyl)isocyanurate, 1,3,5-tris(4-tert-butyl-3-hydroxy-2,6-dimethylbenzyl) isocyanurate, 1,3,5-tris-2[3(3,5-di-tert-butyl-4-hydroxyphenyl) propionyloxy]ethyl isocyanurate, tetrakis[methylene-3-(3,5-di-tert-butyl-4-hydroxyphenyl) propionate]methane, triethyleneglycol-N-bis-3-(3-tert-butyl-4-hydroxy-5-methylphenyl) propionate, triethylene glycol-N-bis-3-(3-tert-butyl-4-hydroxy-5-methylphenyl) acetate, 3,9-bis[2-{3-(3-tert-butyl-4-hydroxy-5-methylphenyl) acetyloxy}-1,1-dimethylethyl]-2,4,8,10-tetraoxaspiro [5,5]undecane, tetrakis[methylene-3-(3-tert-butyl-4-hydroxy-5-methylphenyl)propionate]methane, 1,3,5-trimethyl-2,4,6-tris(3-tert-butyl-4-hydroxy-5-methylbenzyl)benzene and tris(3-tert-butyl-4-hydroxy-5-methylbenzyl)isocyanurate. Out of the above compounds, tetrakis[methylene-3-(3-tert-butyl-4-hydroxy-5-methylphenyl)propionate]methane and octadecyl-3-(3,5-di-tert-butyl-4-hydroxyphenyl) propionate are preferably used. Further, (3,3',3'',5,5',5''-hexa-tert-butyl-α,α',α''-(mesitylene-2,4,6-triyl)tri-p-cresol represented by the following formula (6) and 1,3,5-tris(3,5-di-tert-butyl-4-hydroxybenzyl)-1,3,5-triazine-2,4,6(1H,3H,5H)-trione represented by the following formula (7) are more preferably used as they are excellent in the suppression of the reduction of mechanical properties caused by thermal decomposition at the time of processing.

[Chem 7]

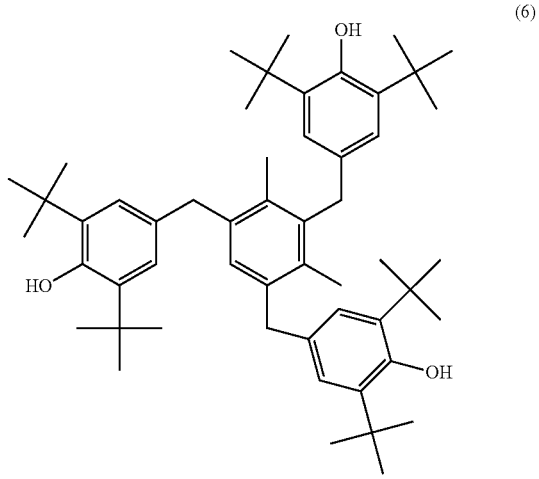

(6)

[Chem 8]

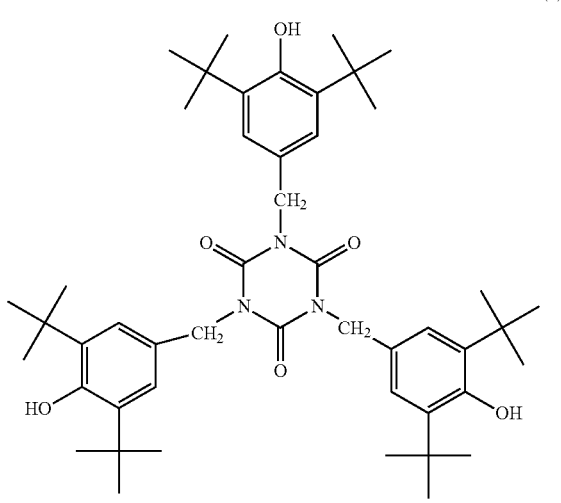

(7)

The above phenol-based stabilizers may be used alone or in combination of two or more. The content of the phenol-based stabilizer is preferably 0.05 to 1.0 part by weight, more preferably 0.07 to 0.8 part by weight, much more preferably 0.1 to 0.5 part by weight based on 100 parts by weight of the total of the components A and B. When the content is lower than 0.05 part by weight, a thermal decomposition suppression effect at the time of processing is not obtained and mechanical properties may deteriorate, and when the content is higher than 1.0 part by weight, mechanical properties may deteriorate as well.

Any one of the phosphorus-based stabilizer and the phenol-based stabilizer is preferably used, and a combination of these is more preferably used. When they are used in combination, 0.01 to 0.5 part by weight of the phosphorus-based stabilizer and 0.01 to 0.5 part by weight of the phenol-based stabilizer are preferably used based on 100 parts by weight of the total of the components A and B.

(iii) Ultraviolet Absorbent

The polycarbonate resin composition of the present invention may comprise an ultraviolet absorbent. Benzophenone-based ultraviolet absorbents include 2,4-dihydroxybenzophenone, 2-hydroxy-4-methoxybenzophenone, 2-hydroxy- 4-octoxybenzophenone, 2-hydroxy-4-benzyloxybenzophenone, 2-hydroxy-4-methoxy-5-sulfoxybenzophenone, 2-hydroxy-4-methoxy-5-sulfoxy trihydride benzophenone, 2,2'-dihydroxy-4-methoxybenzophenone, 2,2',4,4'-tetrahydroxybenzophenone, 2,2'-dihydroxy-4,4'-dimethoxybenzophenone, 2,2'-dihydroxy-4,4'-dimethoxy-5-sodiumsulfoxybenzophenone, bis(5-benzoyl-4-hydroxy-2-methoxyphenyl)methane, 2-hydroxy-4-n-dodecyloxybenzophenone and 2-hydroxy-4-methoxy-2'-carboxybenzophenone.

Benzotriazole-based ultraviolet absorbents include 2-(2-hydroxy-5-methylphenyl)benzotriazole, 2-(2-hydroxy-5-tert-octylphenyl)benzotriazole, 2-(2-hydroxy-3,5-dicumylphenyl)phenylbenzotriazole, 2-(2-hydroxy-3-tert-butyl-5-methylphenyl)-5-chlorobenzotriazole, 2,2'-methylenebis[4-(1,1,3,3-tetramethylbutyl)-6-(2H-benzotriazol-2-yl)phenol], 2-(2-hydroxy-3,5-di-tert-butylphenyl)benzotriazole, 2-(2-hydroxy-3,5-di-tert-butylphenyl)-5-chlorobenzotriazole, 2-(2-hydroxy-3,5-di-tert-amylphenyl)benzotriazole, 2-(2-hydroxy-5-tert-octylphenyl)benzotriazole, 2-(2-hydroxy-5-tert-butylphenyl)benzotriazole, 2-(2-hydroxy-4-octoxyphenyl)benzotriazole, 2,2'-methylenebis(4-cumyl-6-benzotriazolephenyl), 2,2'-p-phenylenebis(1,3-benzoxazin-4-one) and 2-[2-hydroxy-3-(3,4,5,6-tetrahydrophthalimidomethyl)-5-methylphenyl]benzotriazole. Polymers having a 2-hydroxyphenyl-2H-benzotriazole skeleton such as a copolymer of 2-(2'-hydroxy-5-methaeryloxyethylphenyl)-2H-benzotriazole and a vinyl-based monomer copolymerizable with that monomer and a copolymer of 2-(2'-hydroxy-5-acryloxyethypheny)-2H-benzotriazole and a vinyl-based monomer copolymerizable with that monomer are also included.

Hydroxyphenyitriazine-based ultraviolet absorbents include 2-(4,6-diphenyl-1,3,5-triazin-2-yl)-5-hexyloxyphenol, 2-(4,6-diphenyl-1,3,5-triazin-2-yl)-5-methyloxyphenol, 2-(4,6-diphenyl-1,3,5-triazin-2-yl)-5-ethyloxyphenol, 2-(4,6-diphenyl-1,3,5-triazin-2-yl)-5-propyloxyphenol and 2-(4,6-diphenyl-1,3,5-triazin-2-yl)-5-butyloxyphenol. Further, compounds having a 2,4-dimethylphenyl group in place of the phenyl groups of the above compounds, such as 2-(4,6-bis(2,4-dimethylphenyl)-1,3,5-triazin-2-yl)-5-hexyloxyphenol, are further included.

Cyclic iminoester-based ultraviolet absorbents include 2,2'-p-phenylenebis(3,1-benzoxazin-4-one), 2,2'-m-phenylenebis(3,1-benzoxazin-4-one) and 2,2'-p,p'-diphenylenebis(3,1-benzoxazin-4-one).

Cyanoacrylate-based ultraviolet absorbents include 1,3-bis[(2'-cyano-3',3'-diphenylacryloyl)oxy]-2,2-bis[(2-cyano-3,3-diphenylacryloyl)oxy]methyl)propane and 1,3-bis-[(2-cyano-3,3-diphenylacryloyl)oxy]benzene.

The above ultraviolet absorbent may be a polymer type ultraviolet absorbent obtained by copolymerizing an ultraviolet absorbing monomer having the structure of a radically polymerizable monomer compound and/or an optically stable monomer with a monomer such as an alkyl (meth) acrylate. The above ultraviolet absorbing monomer is preferably a compound having a benzotriazole skeleton, a benzophenone skeleton, a triazine skeleton, a cyclic iminoester skeleton or a cyanoacrylate skeleton in the ester substituent of a (meth)acrylic acid ester.

Out of the above compounds, a compound represented by any one of the following formulas (8), (9) and (10) is preferably used in the present invention.

[Chem 9]

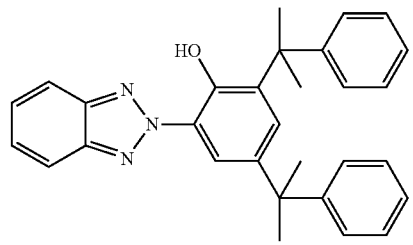

(8)

[Chem 10]

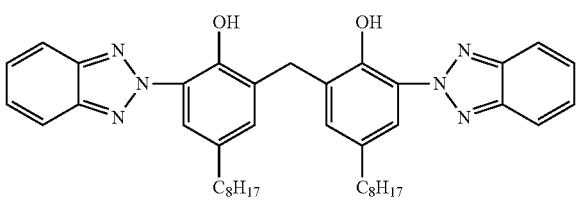

(9)

[Chem 11]

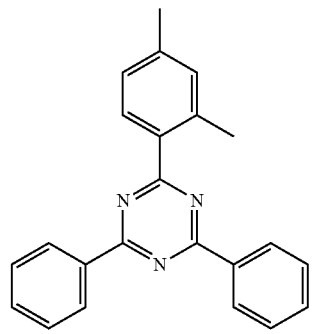

(10)

The above ultraviolet absorbents may be used alone or in combination of two or more.

The content of the ultraviolet absorbent is preferably 0.1 to 2 parts by weight, more preferably 0.12 to 1.5 parts by weight, much more preferably 0.15 to 1 part by weight based on 100 parts by weight of the total of the components A and B. When the content of the ultraviolet absorbent is lower than 0.1 part by weight, satisfactory light resistance may not be developed and when the content is higher than 2 parts by weight, a poor appearance due to the generation of a gas may be obtained and physical properties may deteriorate.

(iv) Hindered Amine-Based Light Stabilizer

The polycarbonate resin composition of the present invention may comprise a hindered amine-based light stabilizer. The hindered amine-based light stabilizer is generally called HALS (Hindered Amine Light Stabilizer), and has a 2,2,6,6-tetramethylpiperidine skeleton in the structure. Examples of the hindered amine-based light stabilizer include 4-acetoxy-2,2,6,6-tetramethylpiperidine, 4-stearoyloxy-2,2,6,6-tetramethylpiperidine, 4-acryloyloxy-2,2,6,6-tetramethylpiperidine, 4-(phenylacetoxy)-2,2,6,6-tetramethylpiperidine, 4-benzoyloxy-2,2,6,6-tetramethylpiperidine, 4-methoxy-2,2,6,6-tetramethylpiperidine, 4-stearyloxy-2,2,6,6-tetramethylpiperidine, 4-cyclohexyloxy-2,2,6,6-tetramethylpiperidine, 4-benzyloxy-2,2,6,6-tetramethylpiperidine, 4-phenoxy-2,2,6,6-tetramethylpiperidine, 4-(ethylcarbamoyloxy)-2,2,6,6-tetramethylpiperidine, 4-(cyclohexylcarbamoyloxy)-2,2,6,6-tetramethylpiperidine, 4-(phenylcarbamoyloxy)-2,2,6,6-tetramethylpiperidine, bis(2,2,6,6- tetramethyl-4-piperidyl)carbonate, bis(2,2,6,6-tetramethyl-4-piperidyl)oxalate, bis(2,2,6,6-tetramethyl-4-piperldyl)malonate, bis(2,2,6,6-tetramethyl-4-piperidyl)sebacate, bis(2,2,6,6-tetramethyl-4-piperidyl)adipate, bis(2,2,6,6-tetramethyl-4-piperidyl)terephthalate, bis(1,2,2,6,6-pentamethyl-4-piperidyl)carbonate, bis(1,2,2,6,6-pentamethyl-4-piperidyl)oxalate, bis(1,2,2,6,6-pentamethyl-4-piperidyl)malonate, bis(1,2,2,6,6-pentamethyl-4-piperidyl)sebacate, bis(1,2,2,6,6-pentamethyl-4-piperidyl)adipate, bis(1,2,2,6,6-pentamethyl-4-piperidyl)terephthalate, N,N'-bis-2,2,6,6-tetramethyl-4-piperidinyl-1,3-benzene dicarboxyamide, 1,2-bis(2,2,6,6-tetramethyl-4-piperidyloxy)ethane, α,α'-bis(2,2,6,6-tetramethyl-4-piperidyloxy)-p-xylene, bis(2,2,6,6-tetramethyl-4-piperidyltolyiene-2,4-dicarbamate, bis(2,2,6,6-tetramethyl-4-piperidyl)-hexamethylene-1,6-dicarbamate, tris(2,2,6,6-tetramethyl-4-piperidyl)-benzene-1,3,5-tricarboxylate, N,N',N'',N'''-tetrakis-(4,6-bis-(butyl-(N-methyl-2,2,6,6-tetramethylpiperidin-4-yl)amino)-triazin-2-yl)-4,7-diazadecane-1,10-diamine, polycondensate of dibutylamine 1,3,5-triazine.N,N'-bis(2,2,6,6-tetramethyl-4-piperidyl)-1,6-hexamethylenediamine and N-(2,2,6,6-tetramethyl-4-piperidyl)butylamine, poly[{6-(1,1,3,3-tetramethylbutyl)amino-1,3,5-triazine-2,4-diyl}{(2,2,6,6-tetramethyl-4-piperidyl)imino} hexamethylene{(2,2,6,6-tetramethyl-4-piperidyl)imino}], tetrakis(2,2,6,6-tetramethyl-4-piperidyl)-1,2,3,4-butane tetracarboxylate, tetrakis(1,2,2,6,6-pentamethyl-4-piperidyl)-1,2,3,4-butane tetracarboxylate, tris(2,2,6,6-tetramethyl-4-piperidyl)-benzene-1,3,4-tricarboxylate, 1-[2-{3-(3,5-di-t-butyl-4-hydroxyphenyl)propionyloxy}butyl]-4-[3-(3,5-di-t-butyl-4-hydroxyphenyl)propionyloxy]2,2,6,6-tetramethylpiperidine and condensate of 1,2,3,4-butane tetracarboxylic acid, 1,2,2,6,6-pentamethyl-4-piperidinol and β,β,β',β'-tetramethyl-3,9-[2,4,8,10-tetraoxaspiro(5,5) undecane]diethanol.

The hindered amine-based light stabilizers are roughly divided into three types according to a site to be bonded to a nitrogen atom in the piperidine skeleton: N—H type (hydrogen is bonded to the nitrogen atom), N—R type (an alkyl group (R) is bonded to the nitrogen atom) and N—OR type (an alkoxy group (OR) is bonded to the nitrogen atom). When it is used for the polycarbonate resin, the N—R type and N—OR type, which have low basicity, are preferably used from the viewpoint of the basicity of the hindered amine-based light stabilizer.

Out of the above compounds, compounds represented by the following formulas (11) and (12) are preferably used in the present invention.

[Chem 12]

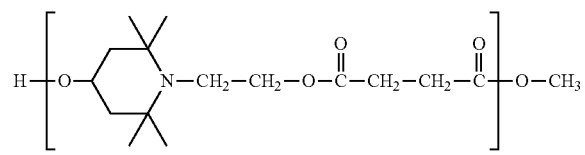

(11)

[Chem 13]

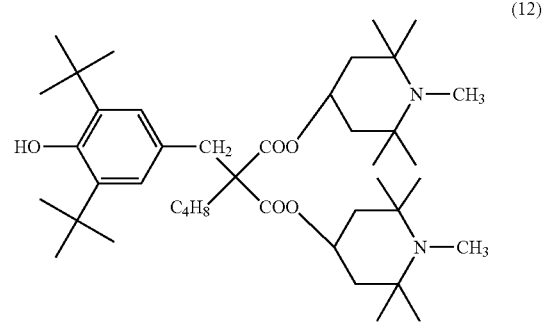

(12)

The hindered amine-based light stabilizer may be used alone or in combination of two or more.

The content of the hindered amine-based light stabilizer is preferably 0 to 1 part by weight, more preferably 0.05 to 1 part by weight, much more preferably 0.08 to 0.7 part by weight, particularly preferably 0.1 to 0.5 part by weight based on 100 parts by weight of the total of the components A and B. When the content of the hindered amine-based light stabilizer is more than 1 part by weight, poor appearance due to the generation of gas, or the deterioration of physical properties due to the decomposition of the polycarbonate resin may occur, which are not preferable. When the content is less than 0.05 part by weight, sufficient light resistance may not develop.

(v) Release Agent

Preferably, the polycarbonate resin composition of the present invention further comprises a release agent in order to improve productivity at the time of molding and suppress the distortion of a molded article. Known release agents may be used. Examples of the release agent include saturated fatty acid esters, unsaturated fatty acid esters, polyolefin-based waxes (such as polyethylene wax, 1-alkene polymers, waxes modified by a functional group-containing compounds may also be used), silicone compounds, fluorine compounds (such as fluorine oils typified by polyfluoroalkyl ethers), paraffin wax and beeswax. Out of these, fatty acid esters are preferred as the release agent. The fatty acid esters are esters of an aliphatic alcohol and an aliphatic carboxylic acid. The aliphatic alcohol may be either a monohydric alcohol or a polyhydric alcohol having 2 or more hydroxyl groups. The number of carbon atoms of the alcohol is 3 to 32, preferably 5 to 30. Examples of the monohydric alcohol include dodecanol, tetradecanol, hexadecanol, octadecanol, eicosanol, tetracosanol, ceryl alcohol and triacontanol. Examples of the polyhydric alcohol include pentaerythritol, dipentaerythritol, tripentaerythritol, polyglycerol(triglycerol to hexaglycerol), ditrimethylolpropane, xylitol, sorbitol and mannitol. In the fatty acid ester of the present invention, a polyhydric alcohol is more preferred.

The aliphatic carboxylic acid has preferably 3 to 32 carbon atoms, particularly preferably 10 to 22 carbon atoms. Examples of the aliphatic carboxylic acid include saturated aliphatic carboxylic acids such as decanoic acid, undecanoic acid, dodecanoic acid, tridecanoic acid, tetradecanoic acid, pentadecanoic acid, hexadecanoic acid (palmitic acid), heptadecanoic acid, octadecanoic acid (stearic acid), nonadecanoic acid, behenic acid, icosanoic acid and docosanoic acid. Unsaturated aliphatic carboxylic acids such as palmitoleic acid, oleic acid, linoleic acid, linolenic acid, eicosenoic acid, eicosapentaenoic acid and cetoleic acid are also included. Out of these, aliphatic carboxylic acids having 14 to 20 carbon atoms are preferred. Saturated aliphatic carboxylic acids are more preferred. Stearic acid and palmitic acid are particularly preferred.

Since the above aliphatic carboxylic acids such as stearic acid and palmitic acid are generally produced from natural oils and fats such as animal oils and fats typified by beef tallow and lard and vegetable oils and fats typified by palm oil and sunflower oil, they are mixtures containing another carboxylic acid component having a different number of carbon atoms. Therefore, even in the production of the aliphatic acid ester of the present invention, an aliphatic carboxylic acid is produced from a natural oil or fat, and therefore an aliphatic carboxylic acid in the form of a mixture containing another carboxylic acid component, especially stearic acid or palmitic acid, is preferably used.

The fatty acid ester of the present invention may be either a partial ester or a full ester. Since the partial ester generally has a large hydroxyl value and easily triggers the decomposition of a resin at a high temperature, the full ester is preferred. The acid value of the fatty acid ester of the present invention is preferably not more than 20, more preferably 4 to 20, much more preferably 4 to 12 from the viewpoint of heat stability. The acid value can be substantially 0. The hydroxyl value of the fatty acid ester is preferably 0.1 to 30. Further, the iodine value is preferably not more than 10. The iodine value can be substantially 0. These properties can be obtained by methods specified in JIS K 0070.

The content of the release agent is preferably 0.005 to 2 parts by weight, more preferably 0.01 to 1 part by weight, much more preferably 0.05 to 0.5 part by weight based on 100 parts by weight of the total of the components A and B. Within the above range, the polycarbonate resin composition has excellent mold releasability and roll releasability. This amount of the fatty acid ester provides a polycarbonate resin composition having excellent mold releasability and roll releasability without impairing a good hue.

(vi) Dye or Pigment

The polycarbonate resin composition of the present invention can provide molded articles having various designs when it further comprises various dyes or pigments. By blending a fluorescent brightener or a luminescent fluorescent dye other than the fluorescent brightener, a good design effect making use of emission color can be provided. A polycarbonate resin composition which is colored and develops a bright color with a trace amount of a dye or a pigment can be provided as well.

Examples of the fluorescent dye (including the fluorescent brightener) used in the present invention include coumalin-based fluorescent dyes, benzopyran-based fluorescent dyes, perylene-based fluorescent dyes, anthraquinone-based fluorescent dyes, thioindigo-based fluorescent dyes, xanthene-based fluorescent dyes, xanthone-based fluorescent dyes, thioxanthene-based fluorescent dyes, thioxanthone-based fluorescent dyes, thiazine-based fluorescent dyes and diaminostilbene-based fluorescent dyes. Out of these, coumalin-based fluorescent dyes, benzopyran-based fluorescent dyes and perylene-based fluorescent dyes are preferred because they have high heat resistance and rarely deteriorate at the time of molding the polycarbonate resin.

Dyes other than the above bluing agents and fluorescent dyes include perylene-based dyes, coumalin-based dyes, thioindigo-based dyes, anthraquinone-based dyes, thioxanthone-based dyes, ferrocyanides such as iron blue, perinone-based dyes, quinoline-based dyes, quinacridone-based dyes, dioxazine-based dyes, isoindolinone-based dyes and phthalocyanine-based dyes. The resin composition of the present invention can obtain a good metallic color when it is blended with a metallic pigment. The metallic pigment is preferably a lamellar filler having a metal film or a metal oxide film.

The content of the above dye or pigment is preferably 0.00001 to 1 part by weight, more preferably 0.00005 to 0.5 part by weight based on 100 parts by weight of the total of the components A and B.

(vii) Other Heat Stabilizers

The polycarbonate resin composition of the present invention may comprise another heat stabilizer except for the above phosphorus-based stabilizer and the above phenol-based stabilizer. The other heat stabilizer is preferably used in combination with any one of the above stabilizer and the antioxidant, particularly preferably both of them. A preferred example of the heat stabilizer is a lactone-based stabilizer typified by a reaction product of 3-hydroxy-5,7-di-tert-butyl-furan-2-one and o-xylene (this stabilizer is detailed in JP-H07-233160A). This compound is marketed under the trade name of Irganox HP-136 (trademark, manufactured by CIBA SPECIALTY CHEMICALS) and may be used. A stabilizer prepared by mixing together the above compound, a phosphite compound and a hindered phenol compound is commercially available. A preferred example of this stabilizer is the Irganox HP-2921 of CIBA SPECIALTY CHEMICALS. This pre-mixed stabilizer may also be used in the present invention. The content of the lactone-based stabilizer is preferably 0.0005 to 0.05 part by weight, more preferably 0.001 to 0.03 part by weight based on 100 parts by weight of the total of the components A and B.

Other stabilizers include sulfur-containing stabilizers such as pentaerythritol tetrakis(3-mercaptopropionate), pentaerythritol tetrakis(3-laurylthiopropionate) and glycerol 3 stearyl thiopropionate. These stabilizers are effective especially when the resin composition is used for rotational molding. The content of the sulfur-containing stabilizer is preferably 0.001 to 0.1 part by weight, more preferably 0.01 to 0.08 part by weight based on 100 parts by weight of the total of the components A and B.

(viii) Filler

The polycarbonate resin composition of the present invention may comprise various fillers as reinforcing filler, as far as it provides the effect of the present invention. Examples includes calcium carbonates, glass fibers, glass beads, glass balloons, glass milled fibers, glass flakes, carbon fibers, carbon flakes, carbon beads, carbon milled fibers, graphite, vapor deposition method hiper-fine carbon fibers (fiber diameter is less than 0.1 μm), carbon nanotube (hollow form; fiber diameter is less than 0.1 μm), fullerene, metal flakes, metal fibers, metal coated glass fibers, metal coated carbon fibers, metal coated glass flakes, silica, metal oxide particles, metal oxide fibers, metal oxide balloons, and any types of whiskers (such as potassium titanate whiskers and aluminum borate whiskers, basic magnesium sulfate). These reinforcing fillers may be used independently, or in combination of at least two of them. The content of the above filler is preferably 0.1 to 60 part by weight, more preferably 0.5 to 50 part by weight based on 100 parts by weight of the total of the components A and B.

(ix) Flame Retardant

The polycarbonate resin composition of the present invention may comprise various compounds known as flame retardant for thermoplastic resins, in particular polycarbonate-based resin. More preferably, the polycarbonate resin composition of the present invention may comprise (i) a halogen-based flame retardant (for example, brominated polycarbonate compound), (ii) a phosphorus-based flame retardant (for example, monophosphate compound, phosphate oligomer compound, phosphonate oligomer compound, phosphonitrile oligomer compound, phosphonic acid amide compound and phosphazene compound), (iii) a metal salt-based flame retardant (for example, organic sulfonic acid alkali (earth) metal salt, boric acid metal salt-based flame retardant and stannic acid metal salt-based flame retardant), and (iv) a silicone-based flame retardant composed of a silicone compound. Not only flame retardancy but also antistatic properties, fluidity, stiffness and thermal stability are improved by mixing a compound used as the flame retardant based on the properties of the compound.

The content of the flame retardant is preferably 0.01 to 30 parts by weight, more preferably 0.05 to 28 parts by weight, much more preferably 0.08 to 25 parts by weight based on 100 parts by weight of the total of the components A and B. When the content of the flame retardant is lower than 0.01 part by weight, satisfactory flame retardancy is not obtained, and when the content is higher than 30 parts by weight, mechanical properties and chemical resistance may greatly degrade.

(x) Light High-Reflection White Pigment

When the polycarbonate resin composition of the present invention is mixed with a light high-reflection white pigment, a light reflection effect can be provided. Examples of the white pigment include zinc sulfide, zinc oxide, barium sulfate, calcium carbonate and baked kaolin. The content of the light high-reflection white pigment is preferably 1 to 30 parts by weight, more preferably 3 to 25 parts by weight based on 100 parts by weight of the total of the components A and B. The above light high-reflection white pigments may be used in combination of two or more.

(xi) Another Resin and Elastomer

Another resin and an elastomer other than the component C may be used in the resin composition of the present invention in small proportions as long as the effect of the present invention is obtained. Examples of the other resin include polyester resins such as polyethylene terephthalate and polybutylene terephthalate, polyamide resins, polyimide resins, polyether imide resins, polyurethane resins, silicone resins, polyphenylene ether resins, polymethacrylate resins, phenol resins and epoxy resins. Examples of the elastomer include isobutylene/isoprene rubber, ethylene/propylene rubber, acrylic elastomers, polyester-based elastomers and polyamide-based elastomers.

(xii) Other Additives

Additives known per se may be mixed with the polycarbonate resin composition of the present invention in small proportions to provide various functions to a molded article and improve the characteristics properties of the molded article. These additives are used in normal amounts as long as the object of the present invention is not impeded. The additives include a sliding agent (such as PTFE particles), a colorant (such as a pigment or dye typified by carbon black), a light diffusing agent (such as acrylic crosslinked particles, silicone crosslinked particles, ultra-thin glass flakes or calcium carbonate particles), a fluorescent dye, an inorganic phosphor (such as a phosphor containing an aluminate as a mother crystal), an antistatic agent, a crystal nucleating agent, inorganic and organic antibacterial agents, an optical catalyst-based antifouling agent (such as particulate titanium oxide or particulate zinc oxide), a radical generator, an infrared absorbent (heat-ray absorbent); and a photochromic agent.

(Production of Thermoplastic Resin Composition)

Any process is employed to produce the thermoplastic resin composition of the present invention. For example, after the components A to C and optionally other additives are fully mixed together by using premixing means such as a V-type mixer, Henschel mixer, mechanochemical device or extrusion mixer, the resulting premixture is granulated by means of an extrusion granulator or a briquetting machine as required, then, melt kneaded by means of a melt kneader typified by a vented double-screw extruder and then pelletized by means of a pelletizer.

Alternatively, a process in which the above components are supplied into a melt kneader typified by a vented double-screw extruder independently or a process in which some of the components are premixed together and supplied into a melt kneader independently from the other components is employed. As for the process in which some of the components are premixed together, for example, after components except for the component A are premixed together, the resulting premixture is mixed with the thermoplastic resin which is the component A or directly supplied into the extruder.

As the premixing method, for example, when the component A is powdery, a method in which some of the powders and additives are blended together to produce a master batch of additives diluted with the powders and this master batch is used may be employed. Further, a method in which one component is supplied at a halfway position of a melt extruder independently may also be employed. When there is a liquid component to be blended, a liquid injection device or a liquid adder may be used to supply it into a melt extruder.

An extruder having a vent from which water contained in the raw materials and a volatile gas generated from the molten kneaded resin can be removed may be preferably used. A vacuum pump is preferably installed to discharge the generated water and the volatile gas to the outside of the extruder from the vent efficiently. A screen for removing foreign matter contained in the extruded raw material may be installed in a zone before the die of the extruder to remove the foreign matter from the resin composition. Examples of the screen include a metal net, a screen changer and a sintered metal plate (such as a disk filter).

Examples of the melt kneader include a Banbury mixer, a kneading roll, a single-screw extruder and a multi-screw extruder having 3 or more screws besides a double-screw extruder.

The resin extruded as described above is pelletized by directly cutting it or by forming a strand therefrom and cutting it with a pelletizer. When the influence of extraneous dust must be reduced at the time of pelletizing, the atmosphere surrounding the extruder is preferably made clean. In the manufacture of the above pellets, it is possible to narrow the form distribution of pellets, reduce the number of miscut products, reduce the amount of fine powders generated at the time of conveyance or transportation and reduce the number of cells (vacuum cells) formed in the strand or pellet by using various methods already proposed for polycarbonate resins for use in optical disks. Thereby, it is possible to increase the molding cycle and reduce the incidence of a defect such as a silver streak. The shape of the pellet may be columnar, rectangular column-like, spherical or other ordinary shape, preferably columnar. The diameter of the column is preferably 1 to 5 mm, more preferably 1.5 to 4 mm, much more preferably 2 to 3.3 mm. The length of the column is preferably 1 to 30 mm, more preferably 2 to 5 mm, much more preferably 2.5 to 3.5 mm.

(Regarding the Medical Box)

The medical box of the present invention refers to a container used for storing and transporting hazardous waste generated from medical institutions and the like. Hazardous waste refers to waste (needles, scalpels, gauze, etc.) which contain or to which there is adhered pathogens that can infect humans. In Japan, medical boxes are marked with a "biohazard symbol" to clearly indicate that they contain hazardous waste, and the specific handling thereof is based on the "Hazardous Waste Management Manual in accordance with the Waste Management Law" issued by the Ministry of the Environment (issued in March 2017). The medical box of the present invention can be usually produced by injection molding the pellet obtained by the method described above. In the injection molding, the medical box can be obtained not only by ordinary molding techniques but also by injection molding techniques such as injection compression molding, injection press molding, gas assist injection molding, foam molding (including what comprises the injection of a super-critical fluid), insert molding, in-mold coating molding, insulated runner molding, quick heating and cooling molding, two-color molding, sandwich molding and super high-speed injection molding according to purpose. The advantages of these molding techniques have already been widely known. Both cold-runner molding and hot-runner molding techniques may also be employed. For example, a container (438 mm×310 mm×554 mm) having a capacity of 50 L can be produced at a cylinder temperature of 280° C./a mold temperature of 80° C. using an injection molding machine having a mold clamping force of 850 tons.

For example, FIG. 1 illustrates an aspect of the medical box of the present invention. This medical box has a container portion and a lid portion, and a biohazard symbol is attached to the container portion.

The embodiment for implementing the present invention is an aggregation of the preferred ranges of the above-mentioned requirements. For example, representative examples are described in the Examples below. Naturally, the present invention is not limited to these embodiments.

EXAMPLES

The present invention is further illustrated by referring to the following examples. Unless otherwise noted, parts in the examples represent parts by weight, and % represents weight %. Evaluations were carried out in accordance with the following methods.
(Evaluation of the Medical Box)
(i) Drop Impact Strength Five % equiv. of water and 15% equiv. of No. 5 silica sand, by volume, were charged into a 50 L capacity container (438 mm×310 mm×554 mm) obtained by the method of the Examples below, a corner of the container was dropped onto a smooth concrete surface from a height of 100 cm, and immediately after dropping, the presence or absence of cracks, ruptures, and tears which could cause the contents to escape from the container was confirmed. The case in which cracks, ruptures, and tears could not be found was evaluated as "Excellent" and the case in which any of there was confirmed was evaluated as "Poor."
(ii) Chemical Resistance A three-point bending evaluation was carried out using an evaluation sample cut into a 130 mm×13 mm strip from the side of a container (438 mm×310 mm×554 mm) having a capacity of 50 L obtained by the method of the Examples below. Specifically, after applying a strain of 1%, a cloth impregnated with Magiclean (manufactured by Kao Corporation) was placed thereon, left to stand at 23° C. for 96 hours, and the presence or absence of changes in appearance was confirmed. Evaluation was performed in accordance with the following criteria.

Excellent: No changes in appearance were observed
Good: The occurrence of fine cracks was observed
Poor: Large cracks which can lead to fracturing were observed
(iii) Heat Resistance Thirteen containers (438 mm×310 mm×554 mm) having a capacity of 50 L obtained by the method of the Examples below were stacked, autoclave sterilization treatment was then carried out with constant-temperature steam (121° C.) for 30 minutes, and the presence or absence of significant deformation of the containers and the fitting with the lid were evaluated.

The case in which there were no problems with regards to significant deformation of the container and fitting with the lid were evaluated as "Excellent", and the case in which there were any of these types of problems was evaluated as "Poor."
(iv) Needle-Penetration Resistance When an evaluation sample cut into a 150 mm×150 mm flat plate from the side of a container (438 mm×310 mm×554 mm) having a capacity of 50 L obtained by the method of the Examples below was pierced with an injection needle under gradual application of load, the case in which the needle bent without penetration was evaluated as "Superior", the case in which the penetration occurred under a load of 30 kN or more was evaluated as "Excellent", and the case in which penetration occurred at a load of less than 30 kN was evaluated as "Poor."

Examples 1 to 9 and Comparative Examples 1 to 4

A mixture having the composition shown in Table 1 and comprising components other than a polypropylene resin as component B and a styrene-based thermoplastic elastomer as component C was supplied from a first supply port of an extruder. The mixtures were obtained by mixing with a twin-cylinder mixer. The propylene-based resin as the component B and a styrene-based thermoplastic elastomer as component C were supplied from a second feed port by using a side feeder. Extrusion was carried out by means of a vented double-screw extruder having a diameter of 30 mm (TEX30α-38.5BW-3V of The Nippon Steel Works, Ltd.) at a screw revolution of 230 rpm, a delivery rate of 25 kg/h and a vent vacuum degree of 3 kPa to perform melt-kneading and to obtain pellets. The extrusion temperature was set to 260° C. from the first feed port to the die. Some of the pellets were dried with a hot air circulation drier at 90 to 100° C. for 6 hours and formed into a container for evaluation (438 mm×310 mm×554 mm) having a capacity of 50 L at a cylinder temperature of 280° C. and a mold temperature of 80° C. by using an injection molding machine having a mold clamping force of 850 tons.
Components represented by symbols in the table are as follows.
(Component A)
A-1: Aromatic polycarbonate resin (a polycarbonate resin powder having a viscosity average molecular weight of 19,700, produced from bisphenol A and phosgene by a conventional method, Panlite L-1225WX (product name), manufactured by Teijin Limited)
A-2: Aromatic polycarbonate resin (a polycarbonate resin powder having a viscosity average molecular weight of 15,000, produced from bisphenol A and phosgene by a conventional method, Panlite CM-1000 (product name), manufactured by Teijin Limited)

(Component B)
B-1: polypropylene resin (homopolymer, MFR: 2 g/10 min (230° C., load of 2.16 kg), PL400A (product name) of Sun Allomer Ltd.)
B-2: polypropylene resin (blockpolymer, MFR: 2 g/10 min (230° C., load of 2.16 kg), PC480A (product name) of Sun Allomer Ltd.)
(Component C)
C-1: styrene-ethylene.propylene-styrene block copolymer (styrene content: 65 wt %, MFR: 0.4 g/10 min (230° C., load of 2.16 kg), SEPTON 2104 (product name) of Kuraray Co., Ltd.)
C-2: styrene-ethylene.butylene-styrene block copolymer (styrene content: 67 wt %, MFR: 2.0 g/10 min (230° C., load of 2.16 kg), TUFTEC H1043 (product name) of Asahi Kasei Chemicals)
(Component D)
D-1: butadiene-based core-shell type graft polymer (graft copolymer having a core-shell structure comprising butadiene rubber as main core component and methyl methacrylate as main shell component, METABLEN E-870A (product name) of Mitsubishi Chemical Co., Ltd.)
D-2: butadiene-based core-shell type graft polymer (graft copolymer having a core-shell structure comprising butadiene rubber as main core component and methyl methacrylate as main shell component, METABLEN E-875A (product name) of Mitsubishi Chemical Co., Ltd.)
D-3: silicone-based core-shell type graft polymer (graft copolymer having a core-shell structure comprising acrylic-silicone composite rubber as main core component and methyl methacrylate as main shell component, METABLEN S-2501 (product name) of Mitsubishi Chemical Co., Ltd.)
(Other Components)
STB: phenol-based heat stabilizer (octadecyl-3-(3,5-di-tert-butyl-4-hydroxyphenyl) propionate, molecular weight of 531, Irganox 1076 (product name) of BASF Japan)

TABLE 1

| | Item | Unit | Examples 1 | 2 | 3 | 4 | 5 | 6 | 7 |
|---|---|---|---|---|---|---|---|---|---|
| Composition | A-1 | p.b.w | 50 | 50 | 50 | 50 | 50 | 50 | 50 |
| | A-2 | " | 15 | 15 | 15 | 15 | 15 | 15 | 15 |
| | B-1 | " | 35 | 35 | 35 | | 35 | 35 | 35 |
| | B-2 | " | | | | 35 | | | |
| | Total | " | 100 | 100 | 100 | 100 | 100 | 100 | 100 |
| | C-1 | " | 18 | 18 | 18 | 18 | 5 | 25 | |
| | C-2 | " | | | | | | | 18 |
| | D-1 | " | | 3.5 | 3.5 | 3.5 | 3.5 | 3.5 | 3.5 |
| | D-2 | " | | | | | | | |
| | D-3 | " | | | | | | | |
| | STB | " | | 0.18 | 0.18 | 0.18 | 0.18 | 0.18 | 0.18 |
| Properties | Drop impact strength | — | Excellent | Excellent | Excellent | Excellent | Excellent | Excellent | Excellant |
| | Chemical resistance | — | Excellent | Excellent | Excellent | Excellent | Excellent | Excellent | Excellent |
| | Heat resistance | — | Excellent | Excellent | Excellent | Excellent | Excellent | Excellent | Excalient |
| | Needle-Penetration Resistance | — | Superior | Superior | Superior | Superior | Superior | Superior | Superior |

| | Item | Unit | Examples 8 | 9 | Comparative Examples 1 | 2 | 3 | 4 |
|---|---|---|---|---|---|---|---|---|
| Composition | A-1 | p.b.w | 50 | 50 | | 77 | 50 | 50 |
| | A-2 | " | 15 | 15 | | 23 | 15 | 15 |
| | B-1 | " | 35 | 35 | 100 | | 35 | 35 |
| | B-2 | " | | | | | | |
| | Total | " | 100 | 100 | 100 | 100 | 100 | 100 |
| | C-1 | " | 18 | 18 | 18 | 18 | | 40 |
| | C-2 | " | | | | | | |
| | D-1 | " | | | | | | |
| | D-2 | " | 3.5 | | | | | |
| | D-3 | " | | 3.5 | | | | |
| | STB | " | 0.18 | 0.18 | | | | |
| Properties | Drop impact strength | — | Excellent | Excellent | Poor | Excellent | Poor | Excellent |
| | Chemical resistance | — | Excellent | Excellent | Excellent | Poor | Poor | Excellent |
| | Heat resistance | — | Excellent | Excellent | Poor | Excellent | Excellent | Poor |
| | Needle-Penetration Resistance | — | Superior | Superior | Poor | Superior | Excellent | Superior | p.b.w. = parts by weight

The invention claimed is:

1. A reusable medical box repeatedly used by autoclaving and for containing a used injection needle, consisting of a polycarbonate resin composition comprising, based on a total of 100 parts by weight of (A) a polycarbonate-based resin (component A) and (B) a polyolefin-based resin (component B), 1 to 30 parts by weight of (C) a styrene-based thermoplastic elastomer (component C).

2. The reusable medical box according to claim 1, wherein a content of styrene units in the component C is 40 to 80 wt %.

3. The reusable medical box according to claim 1, wherein the component B is a polypropylene-based resin.

4. The reusable medical box according to claim 1, wherein a hydrogenated polydiene unit in the component C is a hydrogenated isoprene unit and is a block copolymer having an ethylene-propylene block unit.

5. The reusable medical box according to claim 1, wherein a hydrogenated polydiene unit in the component C is a hydrogenated butadiene unit and is a block copolymer having an ethylene-butylene block unit.

6. The reusable medical box according to claim 1, wherein a hydrogenated polydiene unit in the component C is a partially-hydrogenated butadiene unit and is a block copolymer having a butadiene-butylene block unit.

7. The reusable medical box according to claim 1, wherein a content of the component B is 5 to 50 parts by weight in a total 100 parts by weight of component A and component B.

8. The reusable medical box according to claim 1, further comprising, based on a total of 100 parts by weight of the component A and the component B, 1 to 10 parts by weight of (D) a core-shell graft polymer (component D).

9. The reusable medical box according to claim 1, wherein a melt flow rate (MFR) of the component B and the component C is 0.1 to 10 g/10 min and the ratio of the MFR of the component B and the component C (MFR of component B/MFR of component C) is 0.5 to 10, wherein the MFR is measured in accordance with ISO 1133 at 230 ° C. under a load of 2.16 kg.

* * * * *